US010952993B2

(12) United States Patent
Freeman et al.

(10) Patent No.: US 10,952,993 B2
(45) Date of Patent: Mar. 23, 2021

(54) THERAPEUTIC USES OF GLUCOKINASE ACTIVATORS IN COMBINATION WITH INSULIN OR INSULIN ANALOGS

(71) Applicant: vTv Therapeutics LLC, High Point, NC (US)

(72) Inventors: Jennifer L. R. Freeman, Winston-Salem, NC (US); Maria Carmen Valcarce Lopez, Oak Ridge, NC (US)

(73) Assignee: vTv Therapeutics LLC, High Point, NC (US)

( * ) Notice: Subject to any disclaimer, the term of this patent is extended or adjusted under 35 U.S.C. 154(b) by 9 days.

(21) Appl. No.: 16/741,224

(22) Filed: Jan. 13, 2020

(65) Prior Publication Data
US 2020/0147052 A1 May 14, 2020

Related U.S. Application Data

(63) Continuation of application No. PCT/US2019/036227, filed on Jun. 10, 2019.

(60) Provisional application No. 62/683,772, filed on Jun. 12, 2018, provisional application No. 62/857,753, filed on Jun. 5, 2019.

(51) Int. Cl.
*A61K 31/426* (2006.01)
*A61P 3/10* (2006.01)
*A61K 9/00* (2006.01)

(52) U.S. Cl.
CPC .......... *A61K 31/426* (2013.01); *A61K 9/0053* (2013.01); *A61P 3/10* (2018.01)

(58) Field of Classification Search
CPC ................................ A61K 31/426; A61P 3/10
See application file for complete search history.

(56) References Cited

U.S. PATENT DOCUMENTS

| | | | |
|---|---|---|---|
| 7,598,391 B2 | 10/2009 | Murray et al. | |
| 7,851,636 B2 | 12/2010 | Murray et al. | |
| 7,872,139 B2 | 1/2011 | Murray et al. | |
| 8,263,634 B2 * | 9/2012 | Murray ................ | C07D 277/60 514/396 |
| RE45,183 E | 10/2014 | Murray et al. | |
| 9,359,313 B2 | 6/2016 | Mjalli et al. | |
| 9,855,251 B2 | 1/2018 | Mjalli et al. | |
| 10,004,782 B2 * | 6/2018 | Valcarce Lopez ..... | A61K 38/22 |
| 10,064,846 B2 | 9/2018 | Mjalli et al. | |
| 10,363,244 B2 | 7/2019 | Mjalli et al. | |
| 2018/0311314 A1 | 11/2018 | Lopez et al. | |
| 2019/0046645 A1 | 2/2019 | Benjamin et al. | |

FOREIGN PATENT DOCUMENTS

| WO | WO 2005/066145 A1 | 7/2005 |
|---|---|---|
| WO | WO 2005/123132 A2 | 12/2005 |
| WO | WO 2011/149945 A2 | 12/2011 |
| WO | WO 2013/173417 A2 | 11/2013 |
| WO | WO 2014/137797 A2 | 9/2014 |
| WO | WO 2014/137799 A1 | 9/2014 |

OTHER PUBLICATIONS

Pfuetzner et al., Experimental and Clinical Endocrinology & Diabetes, 1996, 104(1): 25-30 (abstract).*
Johnson et al. Diabetes, 2007, 56:1694-1702.*
Agiostratidou, et al., "Standardizing Clinically Meaningful Outcome Measure Beyond . . . and the T1D Exchange," Diabetes Care 2017;40:1622-1630, American Diabetes Association (2017).
Aicher et al., "ARRY-403, A Novel Glucokinase Activator . . . Activity in Animal Models of Type 2 Diabetes Mellitus," Poster 126—Keystone Symposium: Type 2 Diabetes and Insulin Resistance (J3), Jan. 20-25, 2009, Banff, AB (Array Biopharma).
Amendment No. 6 to Form S-1 Registration Statement for vTv Therapeutics Inc., Jul. 24, 2015. pp. 2-3, 83-84, 96-99.
Battelino, T., et al., "Clinical Targets for Continuous Glucose Monitoring Data" Diabetes Care 42:1593-1603, American Diabetes Association (2019).
Bonadonna et al., " Piragliatin (RO4389620), a Novel Glucokinase Activator, Lowers Plasma Glucose Both in the Postabsorptive State and after a Glucose Challenge in Patients with Type 2 Diabetes Mellitus: A Mechanistic Study," J Clin Endocrinol Metab, 95(11):1-9, The Endocrine Society, United States (2010).
Buse, et al., "Simplici-T1 First Clinical Trial to Test Activation of Glucokinase as an Adjunctive Treatment for Type 1 Diabetes" Late Breaking Abstract, Mar. 2018.
Buse, J.B. et al., "Simplici-T1: First Clinical Trial to Test Activation of Glucokinase as an Adjunctive Treatment for Type 1 Diabetes" Poster presented at the 78th Scientific Session of ADA in Orlando, FL, Jun. 22-26, 2018.
"Classification and Diagnosis of Diabetes: Standards of Medical Care in Diabetes—2018", Diabetes Care 41(Suppl. 1):S13-S27, American Diabetes Association (2018).
Danne, et al., "International Consensus on Use of Continuous Glucose Monitoring," Diabetes Care 40:1631-1640, American Diabetes Association (2017).
Dhanesha, et al., "Treatment with exendin-4 improves the antidiabetic efficacy and reverses hepatic steatosis in glucokinase activator treated db/db mice," European Journal of Pharmacology, 714:188-192, Elsevier, Netherlands (2013).
Di Marco et al. "Synergistic effect of deoxyspergualin (DSP) nd cyclosporin A (CsA) in the prevention of spontaneous autoimmune diabetes in BB rats," Clin Exp Immunol 105:338-343, British Society of Immunology, England (1996).

(Continued)

*Primary Examiner* — Rei Tsang Shiao
(74) *Attorney, Agent, or Firm* — Sterne, Kessler, Goldstein and Fox P.L.L.C.

(57) ABSTRACT

Methods of using glucokinase (GK) activators are generally disclosed herein, particularly in combination with insulin or insulin analogs. In certain aspects, the disclosure provides methods of treating type 1 diabetes that include administering a GK activator in combination with insulin or insulin analogs. Uses of GK activators as a medicament are also disclosed herein, as well as the manufacture of a medicament for such uses.

13 Claims, 6 Drawing Sheets

(56) References Cited

OTHER PUBLICATIONS

Doliba, N. M. et al., "Glucokinase activation repairs defective bioenergetics of islets of Langerhans isolated from type 2 diabetics," Am. J. Physiol. Endocrinol. Metab., 2012, 302: E87-E102, American Physiological Society (2011).

Eiki et al., "Pharmacokinetic and Pharmacodynamic Properties of the Glucokinase Activator MK-0941 in Rodent Models of Type 2 Diabetes and Healthy Dogs," Molecular Pharmacology 80:1156-1165, American Society for Pharmacology and Experimental Therapeutics (2011).

Ericsson et al., "The glucokinase activator AZD6370 decreases fasting and postprandial glucose in type 2 diabetes mellitus patients with effects influenced by dosing regimen and food," Diabetes Research and Clinical Practice 98:436-444 (2012).

Garg SK, et al., "Effects of Sotagliflozin Added to Insulin in Patients with Type 1 Diabetes," N Engl J Med, 377:2337-48 (2017).

Hinklin et al., "ARRY-403, a glucokinase activator with potent glucose-dependent antihyperglycaemic activity in animal modesl of type 2 diabetes mellitus," Diabetologia 52(Suppl):S342 (2009).

Lu, et al., "Characterization of a Novel Glucokinase Activator in Rat and Mouse Models," PLOS One 9(2):88431 (2014).

Matschinsky et al., "Research and Development of Glucokinase Activators for Diabetes Therapy: Theoretical and Practical Aspects," in M. Schwanstecher (ed.), Diabetes—Perspectives in Drug Therapy, Handbook of Experimental Pharmacology 203:357-401, Springer-Verlag GmbH, Germany (2011).

Matschinsky, "GKAs for diabetes therapy: why no clinically useful drug after two decades of trying?," Trends in Pharmacological Sciences, 34(2):90-9, Cell Press, United States (2013).

Matschinsky, F. M. et al. "Glucokinase Activators for Diabetes Therapy" Diabetes Care 34, Supplement 2, S236-S243, American Diabetes Association (2011).

McCarty; M.F., "In type 1 diabetics, high-dose biotin may compensate for low hepatic insulin exposure, promoting a more normal expression of glycolytic and gluconeogenic enzymes and thereby aiding glycemic control," Medical Hypotheses 95:45-8, Eden Press, United States (2016).

McVean et al., "Combination Therapy of ARRY-403 with Metformin, Sitagliptin or Pioglitazone Results in Additive Glucose Lowering in Female ZDF Rats," Poster 104—Keystone Symposium: Type 2 Diabetes and Insulin Resistance (J3), Jan. 20-25, 2009, Banff, AB.

Migoya et al., "The Glucokinase (GK) Activator MK-0599 Lowers Plasma Glucose Concentrations in Healthy Non-Diabetic Subjects" Abstract (2009).

Nakamura A et al., "Control of beta cell function and proliferation in mice stimulated by small-molecule glucokinase activator under various conditions," Diabetologia; Clinical and Experimental Diabetes and Metabolism 55(5):1745-1754, Springer, Germany (2012).

Pal et al., "Recent advances in glucokinase activators for the treatment of type 2 diabetes," Drug Discovery Today 14(15/16):784-792, Elsevier, Netherlands (2009).

Pfefferkorn; J.A. et al., "Strategies for the design of hepatoselective glucokinase activators to treat type 2 diabetes," Expert Opin. Drug Discov. 8(3):319-30, Informa UK. LTD, England (2013).

Polakof, S. "Diabetes Therapy: Novel Patents Targeting the Glucose-Induced Insulin Secretion," Recent Patents on DNA & Gene Sequences, 4(1):1-9, Bentham Science Publishers, Netherlands (2010).

Priyadarsini, R.L. et al., "Glucokinase Activators: A Glucose Sensor Role in Pancreatic Islets and Hepatocyte," International Journal of Pharmacy and Pharmaceutical Sciences 4(2):81-87, Elsevier, Netherlands (2012).

Sands et al., "Sotagliflozin, a Dual SGLT1 and SGLT2 Inhibitor, as Adjunct Therapy to Insulin in Type 1 Diabetes," Diabetes Care, pp. 1-8; Jun. 6, American Diabetes Association (2015).

Sands et al., Supplementary Data for Diabetes Care, pp. 1-8; Jun. 6, American Diabetes Association (2015).

Valcarce C, et al. "Results from the sentinel and learning phase of the Simplici-T1 study, the first clinical trial to test activation of glucokinase as an adjunctive treatment for type 1 diabetes." Presented at the 55th EASD conference, Sep. 18, 2019, Barcelona, Spain.

Valcarce, C. "The Importance of Tissue Selectivity and Preservation of the Physiological Regulation when Targeting Key Metabolic Regulators as Glucokinase," Poster presented at the Keystone Conference in La Jolla, CA, Apr. 17-20, 2016.

Valcarce, C. and Fong, T.—TTP399, A Liver Selective Glucokinase Activator Increases Efficacy of Currently Marketed Therapies for Type 2 Diabetes. Jun. 2015. ADA 75th Scientific Sessions, Boston (1271-P).

Valcarce, C. and Fong, T. Abstract—TTP399, A Liver Selective Glucokinase Activator Increases Efficacy of Currently Marketed Therapies for Type 2 Diabetes. Jun. 2015. ADA 75th Scientific Sessions, Boston (1271-P).

Valcarce, C. et al.—TTP399, A Liver Selective Glucokinase Activator (GKA) the Preserves the Physiological Regulation of Glucokinase (GK) by GK Regulatory Protein (GKRP). Jun. 2015. ADA 75th Scientific Sessions, Boston (1168-P).

Valcarce, C., et al.—TTP399, A Liver-Selective Glucose Kinase Activator (GKA), Lowers Glucose and Does NOT Increase Lipids in Subjects with Type 2 Diabetes Mellitus (T2DM). Jun. 2014. ADA 74th Scientific Sessions. (122-OR).

Valcarce, C., et al. Abstract—TTP399, A Liver Selective Glucokinase Activator (GKA) the Preserves the Physiological Regulation of Glucokinase (GK) by GK Regulatory Protein (GKRP). Jun. 2015. ADA 75th Scientific Sessions, Boston (1168-P).

Valcarce, C., et al., Abstract—TTP399, a Liver-Selective Glucose Kinase Activator (GKA), Lowers Glucose and Does NOT Increase Lipids in Subjects with Type 2 Diabetes Mellitus (T2DM). Jun. 2014. ADA 74th Scientific Sessions. (122-OR).

Valcarce, et al., "TTP399, a Novel, Liver Selective Glucokinase Activator: Results from a 10 day Pilot Study in Patients with type 2 Diabetes Mellitus *(T2DM) Naive to Drug," Poster presented at the 76th Scientific Sessions of the ADA in New Orleans, LA, Jun. 11-13, 2016.

Vella et al., "Targeting hepatic glucokinase to treat diabetes with TTP399, a hepatoselective glucokinase activator," Science Translational Medicine, vol. 11 (2019).

Vella, A et al., "TTP399: A liver-selective . . . 6-Month Phase 2 Study" presented at the 17th Annual Rachmiel Levine-Arthur Riggs Diabetes Research Symposium, Endocrine Society ENDO2017 Conference, Orlando, Florida, Mar. 27-Apr. 4, 2017.

Vella, A. et al., Abstract "TTP399: A liver-selective . . . 6-Month Phase 2 Study" presented at the 17th Annual Rachmiel Levine-Arthur Riggs Diabetes Research Symposium, Endocrine Society ENDO2017 Conference, Orlando, Florida, Mar. 27-Apr. 4, 2017.

vTv Therapeutics—Investor Presentation—Jul. 2015. Slides 19-24.

Mathieu; C. et al., "Glucose Variable in Type 1 Diabetes Studies With Dapagliflozin: Pooled Analysis of Continuous Glucose Monitoring Data From DEPICT-1 and 2," Diabetes Care 42:1081-1087 and supplementary data, American Diabetes Association (2019).

Rosenstock; J. et al., "Empagliflozin As Adjunctive to Insulin Therapy in Type 1 Diabetes: The EASE Trials," Diabetes Care 41:2560-9, American Diabetes Association (2018).

Wolfsdorf; J. et al., "SGLT Inhibitors for Type 1 Diabetes: Proceed with Extreme Caution," Diabetes Care 42:991-3, American Diabetes Association (2019).

Buse, et al., "The Simplici-T1 Trial: Glucokinase activator (GKA) TTP399 improves glycemic control in patients with type 1 diabetes (T1D)" Poster presented at the 80th Scientific Session of ADA, Jun. 12-16, 2020, 10 pages.

Valcarce, et al. "The Simplici-T1 Trial: Relationship Between Glycemic Control and Insulin Dose" Poster presented at the 80th Scientific Session of ADA, Jun. 12-16, 2020, 9 pages.

Freeman, J., et al., "Mechanism matters: preliminary evidence that activation of glucokinase by TTP399 does not increase plasma or urine ketones in type 1 diabetes," P51, presented at the 56th European Association for the Study of Diabetes Conference—Virtual, Sep. 22, 2020, 15 pages.

Valcarce, C., "Selective Activation of Glucokinase (GK) in the Liver: Improves Glycemic Control and Reduces Insulin Need as

(56) References Cited

OTHER PUBLICATIONS

Well as Risk of Ketoacidosis in Type 1 Diabetic Minipigs," presented at the Keystone Symposia on Diabetes, Jan. 22-26, 2017, Keystone, Colorado, 1 page.

Valcarce, C., et al., "The Simplici-T1 trial: Activation of glucokinase by TTP399 improves glycemic control in patients with T1DM," P50, presented at the 56th European Association for the Study of Diabetes Conference—Virtual, Sep. 22, 2020, 17 pages.

International Preliminary Report on Patentability for International Application No. PCT/US2019/036227, The International Bureau of WIPO, Switzerland, dated Dec. 15, 2020, 5 pages.

* cited by examiner

THERAPEUTIC USES OF GLUCOKINASE ACTIVATORS IN COMBINATION WITH INSULIN OR INSULIN ANALOGS

CROSS-REFERENCE TO RELATED APPLICATIONS

This application is a continuation of International Application No. PCT/US2019/036227, filed Jun. 10, 2019, which claims benefit of U.S. Provisional Application Nos. 62/683,772, filed Jun. 12, 2018, and 62/857,753, filed Jun. 5, 2019.

TECHNICAL FIELD

Methods of using glucokinase (GK) activators are generally disclosed herein, particularly in combination with insulin or insulin analogs. In certain aspects, the disclosure provides methods of treating type 1 diabetes that include administering a GK activator in combination with insulin or insulin analogs. In certain other aspects, the disclosure provides methods of treating related conditions and improving glycemic control, such as increasing the percentage of time a subject is in target blood-glucose range, decreasing the percentage of time a subject is in hypoglycemic or hyperglycemic range, reducing body weight, reducing glycated hemoglobin levels, reducing the occurrence of ketoacidosis, lowering mean daily blood-glucose levels, reducing total daily bolus insulin dose, reducing total daily basal insulin dose, reducing total daily insulin dose, reducing total number of daily insulin injections, reducing total number of daily basal insulin injections, reducing total number of bolus insulin injections, reducing total daily bolus insulin dose at each meal, reducing number of hypoglycemic events over a period of time, reducing number of severe hypoglycemic events over a period of time. Uses of GK activators as a medicament are also disclosed herein, as well as the manufacture of a medicament for such uses.

BACKGROUND

Diabetes mellitus type 1 (type 1 diabetes) is a chronic condition that results from the autoimmune destruction of the insulin-producing beta cells in the pancreas. As a result, persons suffering from type 1 diabetes cannot produce sufficient insulin to permit them to regulate blood-glucose levels properly. Thus, without treatment, they would likely suffer from acute conditions resulting from extremely high blood-glucose. But, even with treatment, persons suffering from type 1 diabetes can still experience fluctuations in blood-glucose levels that result in acute conditions (such as hyperglycemia and hypoglycemia) and that can eventually increase risk of chronic conditions, such as heart disease, stroke, blindness (due to diabetic retinopathy), kidney failure, and poor blood circulation to the limbs (which can result in the need to amputate limbs that no longer benefit from sufficient circulation).

Type 1 diabetes can generally only be managed through the administration of insulin or insulin analogs. Recent decades have witnessed an expansion in the different kinds of insulin that is available, including rapid-acting insulin, short-acting insulin, intermediate-acting insulin, and long-acting insulin. Further, devices have recently come to market that offer continuous glucose monitoring, coupled with a pump for making real-time adjustments to insulin dosing. Many pharmaceutical drug therapies useful for treating non-insulin dependent diabetes have shown low or no effectiveness at treating type 1 diabetes. That is because many pharmaceutical drug therapies rely on the body's ability to make endogenous insulin. Thus, such therapies are of little use in treating type 1 diabetes, because type 1 diabetics have little or no ability to make and secrete endogenous insulin.

Thus, there is a continuing need to develop effective pharmaceutical compounds that can assist in the management of type 1 diabetes without relying on the production of endogenous insulin.

SUMMARY

The present disclosure generally provides methods of treating type 1 diabetes and related conditions using combinations of a liver-selective glucokinase (GK) activator and insulin or analogs thereof. It was surprisingly discovered that activation of GK in the liver GK (versus GK in the pancreas or brain) could improve efficacy of insulin therapy, improve glycemic control and/or simplify treatment regimens in type 1 diabetics. Therefore, it was discovered that one could achieve these results, in certain respects, by coupling insulin administration with administration of a liver-selective GK activator.

Glucokinase (GK) is an enzyme that, among other things, facilitates phosphorylation of glucose to glucose-6-phosphate. In vertebrates, GK-mediated glucose phosphorylation typically occurs in cells in the liver, pancreas, gut, and brain. In each of these organs, GK can play a role in regulating carbohydrate metabolism by acting as a glucose sensor, triggering shifts in metabolism or cell function in response to rising and/or falling levels of blood glucose. Small-molecule GK activators are useful because they can enhance the rate of glucose phosphorylation, and thereby reduce the amount of glucose in the blood.

Methods of Treatment

In a first aspect, the disclosure provides methods of treating type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of increasing the percentage of time in target blood-glucose range in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the total daily bolus insulin dose in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of lowering mean daily blood-glucose in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing blood glucagon levels in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of lowering glycated hemoglobin levels in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the percentage of time in hypoglycemic range in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the percentage of time in hyperglycemic range in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the incidence, duration, or likelihood of diabetic ketoacidosis in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the incidence, duration, or likelihood of diabetic ketosis in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing one or more metabolic ketones in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing body weight in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing total daily basal insulin dose in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing total daily insulin dose in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the total number of daily insulin injections in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing total number of daily basal insulin injections in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the total number of daily bolus insulin injections in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing total daily bolus insulin dose at each meal in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the number of hypoglycemic events over a period of time in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of reducing the number of severe hypoglycemic events over a period of time in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides methods of treatment to achieve any of the previous improvements in glycemic control (such as reducing time in hypoglycemic range or reduction in number of hypoglycemic or severe hypoglycemic events) in combination with either no decrease in level of HbA1c in the subject or only a slight increase (0.1%, 0.2%, or 0.3%) in HbA1c in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

Uses of Combination

In another aspect, the disclosure provides uses of a liver-selective glucokinase activator in combination with insulin or an analog thereof for treating type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for increasing the percentage of time in target blood-glucose range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing total daily bolus insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for lowering mean daily blood-glucose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing blood-glucagon levels in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for lowering glycated hemoglobin levels in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the percentage of time in hypoglycemic range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the percentage of time in hyperglycemic range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the incidence, duration, or likelihood of diabetic ketoacidosis in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the incidence, duration, or likelihood of diabetic ketosis in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing one or more metabolic ketones in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing body weight in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing total daily basal insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing total daily insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the total number of daily insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the total number of daily basal insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the total number of daily bolus insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing total daily bolus insulin dose at each meal in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the number of hypoglycemic events over a period of time in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof for reducing the number of severe hypoglycemic events over a period of time in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in combination with insulin or an analog thereof to achieve any of the previous improvements in glycemic control, such as reducing time in hypoglycemic or reduction in number of hypoglycemic or severe hypoglycemic events) in combination with either no decrease in level of HbA1c in the subject or only a slight increase in HbA1c in a subject having type 1 diabetes, the methods comprising administering to a subject in need thereof a liver-selective glucokinase activator in combination with insulin or an analog thereof. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

Manufacture of a Medicament

In another aspect, the disclosure provides uses of a liver-selective glucokinase activator in the manufacture of a medicament for use in combination with insulin or an analog thereof for treating type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for increasing the percentage of time in target blood-glucose range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing total daily bolus insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for lowering mean daily blood-glucose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing blood-glucagon levels in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for lowering glycated hemoglobin levels in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the percentage of time in hypoglycemic range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the percentage of time in hyperglycemic range in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the incidence, duration, or likelihood of diabetic ketoacidosis in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the incidence, duration, or likelihood of diabetic ketosis in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing one or more metabolic ketones in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing body weight in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing total daily basal insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing total daily insulin dose in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the total number of daily insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing total number of daily basal insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the total number of daily bolus insulin injections in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing total daily bolus insulin dose at each meal in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the number of hypoglycemic events over a period of time in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof for reducing the number of severe hypoglycemic events over a period of time in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

In another aspect, the disclosure provides uses of a liver-selective glucokinase activator in the manufacture of a medicament for use in combination with insulin or an analog thereof to achieve any of the previous improvements in glycemic control (such as reducing time in hypoglycemic range or reduction in number of hypoglycemic or severe hypoglycemic events) in combination with either no decrease in level of HbA1c in the subject or only a slight increase in HbA1c in a subject having type 1 diabetes. In some embodiments thereof, the liver-selective glucokinase activator is {2-[3-cyclohexyl-3-(trans-4-propoxy-cyclohexyl)-ureido]-thiazol-5-ylsulfanyl}-acetic acid or a pharmaceutically acceptable salt thereof.

Other aspects and embodiments are set forth in the foregoing drawings, detailed description, and claims.

DETAILED DESCRIPTION

Figure 1:
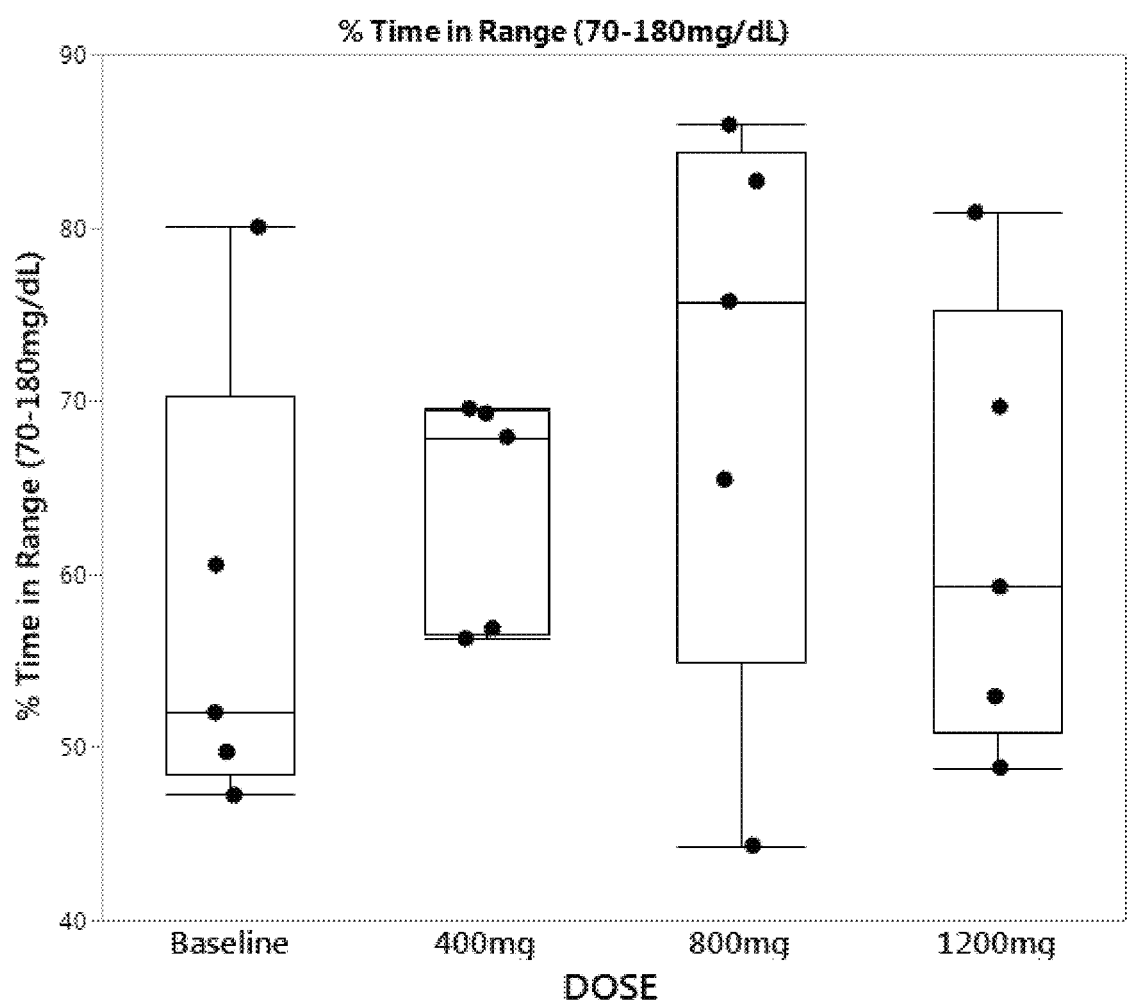
FIG. 1 displays the percentage of time each subject's blood glucose level was between 70 and 180 mg/dL at each dose (400, 800, and 1200 mg/day of UT-1) and for baseline, where each data point represents the median of four days (days 3-6) at each dose for each subject.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (e.g., self-administration).

As used herein, "treat" or "treating" or "treatment" can refer to one or more of: delaying the progress of a disease, disorder, or condition; controlling a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In some embodiments, the "subject" is a human. In some such embodiments, the "subject" is a human who exhibits one or more symptoms characteristic of a disease, disorder, or condition. The term "subject" does not require one to have any particular status with respect to a hospital, clinic, or research facility (e.g., as an admitted patient, a study participant, or the like).

As used herein, the terms "blood glucose level", "blood sugar level", "plasma glucose level" and "blood sugar concentration" refer to the amount of glucose present in the blood of a subject, and these terms may be used interchangeably. Blood glucose levels are typically measured in units of mg/dL or mmol/L.

As used herein, the term "metabolic ketone" refers to any compound produced by metabolization of fatty acids, such as by liver enzymes, and includes, but is not limited to, acetoacetate (AcAc), beta-hydroxybutyrate (BHB), and acetone.

As used herein, the term "hypoglycemia" refers to a blood glucose level below a normal level for a subject. In a human, hypoglycemia may be defined as a blood glucose level of less than 70 mg/dL. In an embodiment, hypoglycemia in a human is a blood glucose level of less than 70 mg/dL and greater than or equal to 54 mg/dL.

As used herein, the term "severe hypoglycemia" refers to a blood glucose level significantly below a normal level for a subject. In a human, severe hypoglycemia may be defined as a blood glucose level of less than 54 mg/dL.

As used herein, the term "hypoglycemic event" refers to a blood glucose level below normal level for a subject for a period of time. In an embodiment, a hypoglycemic event may occur upon a single measure of blood glucose level below normal through self-monitoring blood glucose (SMBG). In other embodiments, where blood glucose levels are continuously monitored, a hypoglycemic event may occur over a period of time such as where the blood glucose level is continuously below normal for at least 1, 2, 3, 4, 5, 6, 7, 9, 10, 12, 15, 20, 25, 30, 60, or 120 minutes. In an embodiment, in a human a hypoglycemic event may be defined as a blood glucose level of less than 70 mg/dL for a period of time or a single SMBG measurement. In another embodiment, in a human a hypoglycemic event may be defined as a blood glucose level of less than 70 mg/dL and greater than or equal to 54 mg/dL for a period of time or a single SMBG measurement. The end of the hypoglycemic event may occur after a subject's blood glucose level continuously rises above a threshold for a period of time. For example, blood glucose level may need to be continuously above a threshold for at least 1, 2, 3, 4, 5, 6, 7, 9, 10, 12, 15, 20, 25, 30, 60, or 120 minutes to mark the end of a hypoglycemic event. In an embodiment, in a human the end of a hypoglycemic event may be defined as a blood glucose level of greater than 70 mg/dL for a period of time or a single SMBG measurement.

As used herein, the term "severe hypoglycemic event" refers to a blood glucose level significantly below a normal level for a subject for a period of time. In an embodiment, a severe hypoglycemic event may occur upon a single measure of blood glucose level significantly below normal through self-monitoring blood glucose (SMBG). In other embodiments, where blood glucose levels are continuously monitored, a severe hypoglycemic event may occur over a period of time such as where the blood glucose level is continuously below normal for at least 1, 2, 3, 4, 5, 6, 7, 9, 10, 12, 15, 20, 25, 30, 60, or 120 minutes. In an embodiment, in a human a severe hypoglycemic event may be defined as a blood glucose level of less than 54 mg/dL for a period of time or a single SMBG measurement. The end of the severe hypoglycemic event may occur after a subject's blood glucose level continuously rises above a threshold for a period of time or a single SMBG measurement. For example, blood glucose level may need to be continuously above a threshold for at least 1, 2, 3, 4, 5, 6, 7, 9, 10, 12, 15, 20, 25, 30, 60, or 120 minutes to mark the end of a hypoglycemic event. In an embodiment, in a human the end of a severe hypoglycemic event may be defined as a blood glucose level of greater than or equal to 54 mg/dL for a period of time or a single SMBG measurement.

As used herein, the term "hyperglycemia" refers to a blood glucose level above the normal level in a subject. In a human, hyperglycemia may be defined as a blood glucose level of greater than 180 mg/dL. In an embodiment, hyperglycemia in a human is a blood glucose level of greater than 180 mg/dL and less than or equal to 250 mg/dL.

As used herein, the term "severe hyperglycemia" refers to a blood glucose level significantly above the normal level in a subject. In a human, severe hyperglycemia may be defined as a blood glucose level of greater than 250 mg/dL.

As used herein, the term "hyperglycemic event" refers to a blood glucose level above normal level for a subject for a period of time. In an embodiment, a hyperglycemic event may occur upon a single measure of blood glucose level above normal through self-monitoring blood glucose (SMBG). In other embodiments, where blood glucose levels are continuously monitored, a hyperglycemic event may occur over a period of time such as where the blood glucose level is continuously above normal for at least 1, 2, 3, 4, 5, 6, 7, 9, 10, 12, 15, 20, 25, 30, 60, or 120 minutes. In an embodiment, in a human a hyperglycemic event may be defined as a blood glucose level of greater than 180 mg/dL for a period of time or a single SMBG measurement. In another embodiment, in a human a hyperglycemic event may be defined as a blood glucose level of greater than 180 mg/dL and less than or equal to 250 mg/dL for a period of time or a single SMBG measurement. The end of the hyperglycemic event may occur after a subject's blood glucose level continuously falls below a threshold for a period of time. For example, blood glucose level may need to be continuously below a threshold for at least 1, 2, 3, 4, 5, 6, 7, 9, 10, 12, 15, 20, 25, 30, 60, or 120 minutes to mark the end of a hyperglycemic event. In an embodiment, in a human the end of a hyperglycemic event may be defined as a blood glucose level of less than 180 mg/dL for a period of time or a single SMBG measurement.

As used herein, the term "severe hyperglycemic event" refers to a blood glucose level significantly above a normal level for a subject for a period of time. In an embodiment, a severe hyperglycemic event may occur upon a single measure of blood glucose level significantly above normal through self-monitoring blood glucose (SMBG). In other embodiments, where blood glucose levels are continuously monitored, a severe hyperglycemic event may occur over a period of time such as where the blood glucose level is continuously above normal for at least 1, 2, 3, 4, 5, 6, 7, 9, 10, 12, 15, 20, 25, 30, 60, or 120 minutes. In an embodiment, in a human a severe hyperglycemic event may be defined as a blood glucose level of greater than 250 mg/dL for a period of time or a single SMBG measurement. The end of the severe hyperglycemic event may occur after a subject's blood glucose level continuously falls below a threshold for a period of time or a single SMBG measurement. For example, blood glucose level may need to be continuously below a threshold for at least 1, 2, 3, 4, 5, 6, 7, 9, 10, 12, 15, 20, 25, 30, 60, or 120 minutes to mark the end of a hyperglycemic event. In an embodiment, in a human the end of a severe hyperglycemic event may be defined as a blood glucose level of less than or equal to 250 mg/dL for a period of time or a single SMBG measurement.

As used herein, the term "bolus insulin dose" is an insulin dose that is specifically administered in a subject immediately before or immediately after or around meal times to keep blood glucose levels under control following a meal. A bolus insulin dose should act quickly and so short-acting insulin, rapid-acting insulin, or combinations thereof are often used in bolus insulin doses.

As used herein, the term "basal insulin dose" is an insulin dose that is administered to a subject to keep blood glucose levels within acceptable ranges during period of fasting such as between meals or during periods of sleeping. A basal insulin dose is often administered once or twice a day, but may be administered more often. Basal insulin doses need to act over a relatively long period of time (such as several hours) and therefore a basal insulin dose often comprises a long-acting insulin, an intermediate-acting, or a mixture of a long-acting and intermediate-acting insulin.

As used herein, the term "baseline" refers to a period prior treatment and the associated level or value of an item being measured during that pre-treatment period. In an embodiment, the pre-treatment period may be a continuous period 1 day, 2 days, 3 days, 4 days, 5 days, 6 days, or more before treatment. The pre-treatment period may end immediately before treatment begins or the pre-treatment period may be a continuous period that ends at least 1 day, 2 days, 3 days or more before treatment begins.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

As used herein, the term "pharmaceutically acceptable salt" refers to a salt of a compound which are generally prepared by reacting the free base with a suitable organic or inorganic acid or by reacting the acid with a suitable organic or inorganic base. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, glucepate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate, and the like. In certain embodiments, the GK activator is in the form of hydrochloride acid salt. In other embodiments, the GK activator is in the form of a free acid.

As used herein, the unit term "mg/kg" refers to the mass (measured in mg) of compound administered to a subject per the mass (measured in kg) of the subject. For example, "administering 1.0 mg/kg daily to a subject" refers to administering 170 mg daily to a subject having a mass of 170 kg.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, a "GK activator" is a compound that activates GK in a subject, such as a human, in direct or indirect response to the presence of the compound, or a metabolite thereof, in the subject. WO 2005/066145 provides a non-limiting list of compounds that are GK activators. Further, GK activators may activate GK wherever GK is present, but some may selectively activate GK in certain systems or organs. For the treatment of reduction of blood glucose levels, one is generally concerned with GK activation in the pancreas and/or the liver. Where a GK activator is a liver-selective GK activator, the GK activator directly or indirectly increases glucose utilization in the liver (hepatic cells) at doses that do not induce a substantial increase in insulin secretion by the pancreas (beta-cells) in response to glucose (e.g., less than a 25% increase, or less than a 15% increase, or less than a 10% increase, or less than a 5% increase, or less than a 3% increase in insulin secretion by the pancreas in response to glucose) or that do not induce a substantial increase in GK activity in other systems or organs such the brain or CNS. In some embodiments, the liver-selective GK activator is {2-[3-cyclohexyl-3-(trans-4-propoxy-cyclohexyl)-ureido]-thiazol-5-ylsulfanyl}-acetic acid or a pharmaceutically acceptable salt thereof.

Other terms are defined in other portions of this description, even though not included in this subsection.

Combinations of GK Activators and Insulin

In one or more of the aforementioned aspects, the disclosure provides methods of administering GK activators (or, in some embodiments, liver-selective GK activators) to subjects in need thereof. In general, such methods include administering to a subject in need thereof a GK activator in combination with insulin or an analog thereof.

Any suitable GK activator or liver-selective GK activator can be used. In some embodiments, the liver-selective GK activator is {2-[3-cyclohexyl-3-(trans-4-propoxy-cyclohexyl)-ureido]-thiazol-5-ylsulfanyl}-acetic acid or a pharmaceutically acceptable salt thereof. In some further embodiments, the liver-selective GK activator is {2-[3-cyclohexyl-3-(trans-4-propoxy-cyclohexyl)-ureido]-thiazol-5-ylsulfanyl}-acetic acid. In some other embodiments, the liver-selective GK activator is a pharmaceutically acceptable salt of {2-[3-cyclohexyl-3-(trans-4-propoxy-cyclohexyl)-ureido]-thiazol-5-ylsulfanyl}-acetic acid.

The GK activator can be administered in any suitable way, including subcutaneous delivery, intravenous delivery, intramuscular delivery, intracisternal delivery, delivery by infusion techniques, transdermal delivery, oral delivery, nasal delivery, and rectal delivery. In some embodiments of any of the aforementioned embodiments, the administering comprises orally administering the liver-selective GK activator. Suitable oral dosage forms are described in further detail below.

The liver-selective GK activator is administered in combination with insulin or an analog thereof. In this context, "in combination with" does not necessarily imply that the agents are administered on the same schedule or as part of a common dosage form. In some instances, these medications may be once-daily or once-weekly medications, and may be administered by different means.

Insulin

The insulin or analog thereof may be administered in any suitable means, including, but not limited to, oral administration (via gut or lungs), subcutaneous administration (such as continuous subcutaneous insulin infusion), administration by injection. In some further embodiments, the insulin or analog thereof is administered by subcutaneous administration, or administration by injection. In another embodiment, insulin or analog thereof is administered by two different routes.

Any suitable form of insulin or its analogs can be used. These include, but are not limited to, rapid-acting insulin, regular- or short-acting insulin, intermediate-acting insulin, and long-acting insulin. When injected subcutaneously, rapid-acting insulin generally reaches the blood stream about 15 minutes after injection and is effective for 2 to 4 hours. Types of rapid-acting insulin include: Insulin glulisine (Apidra), insulin lispro (Humalog), and insulin aspart (NovoLog). When injected subcutaneously, regular- or short-acting insulin generally reach the bloodstream within 30 minutes after injection and is effective for approximately 3 to 6 hours. Types of regular- or short acting insulin included: Humulin R, Novolin R. When injected subcutaneously, intermediate-acting insulin generally reaches the bloodstream about 2 to 4 hours after injection and is effective for about 12 to 18 hours. Types of intermediate-acting insulin include: NPH (Humulin N, Novolin N). When injected subcutaneously, long-acting insulin generally reaches the bloodstream several hours after injection and is effective over a 24-hour period. Types of long-acting insulin include: Insulin detemir (Levemir) and insulin glargine (Lantus). In certain embodiments, the administering comprises administering to the subject in need thereof the liver-selective glucokinase activator in combination with an insulin, such as a rapid-acting insulin, a short-acting insulin, an intermediate-acting insulin, a long-acting insulin, or a combination of insulins. In some embodiments, the combination of insulin administered may comprise a rapid-acting and a short-acting insulin. In other embodiments, the combination of insulin administered may comprise an intermediate-acting insulin and a long-acting insulin. In other embodiments, the combination of insulin administered may comprise any combination of two, three, or four types of insulin. In some other embodiments, the administering comprises administering to a subject in need thereof a liver-selective glucokinase activator in combination with insulin lispro, insulin aspart, insulin glulisine, isophane insulin, insulin zinc, insulin glargine, insulin detemir, or any combinations thereof.

Subjects

The disclosed methods may be carried out on any suitable subjects, including humans, horses, cows, sheep, pigs, mice, rats, dogs, cats, and primates such as chimpanzees, gorillas, and rhesus monkeys. In some embodiments, the subject is a human.

In the methods disclosed herein, the subject is a subject in need of the administration of the treatment. In some embodiments, this includes a subject exhibiting one or more of the following symptoms: (i) a fasting blood-glucose concentration of greater than 100 mg/dL, or greater than 110 mg/dL, or greater 100 or 110 mg/mL and less than 125 mg/dL; (ii) a 2-hour postprandial plasma-glucose level greater than 140 mg/dL or a 3-hour postprandial plasma-glucose level greater than 140 mg/dL; (iv) having an HbA1c value equal to or greater than 5.7%, 6.5%, 7.0%, 7.5% or 8.0%; or (v) persistent presence of two or more islet antibodies.

The nature of the subject's need depends on the therapeutic goals. In some embodiments of any of the foregoing embodiments, the subject exhibits elevated levels of glycated hemoglobin in its blood, for example, elevated levels of HbA1c in its blood. In some such embodiments, administering the liver-selective GK activator in combination with insulin or an analog thereof is carried out to reduce the subject's glycated hemoglobin levels, such as the subject's HbA1c levels. In some embodiments, other measures of glycemic control are achieved (such as reduction of time in hypoglycemic range or reduction in number of hypoglycemic or severe hypoglycemic events) in combination with a reduction in HbA1c or without any reduction in HbA1c levels or with a slight increase in HbA1c levels.

In some other embodiments, the subject exhibits one or more symptoms consistent with type 1 diabetes. In some such embodiments, administering the liver-selective GK activator in combination with insulin or an analog is carried out to treat type 1 diabetes (including treating one or more of the symptoms associated therewith). In some other embodiments, the subject has elevated body mass, or in some cases, obesity. In some such embodiments, administering the liver-selective GK activator in combination with insulin or an analog thereof is carried out to reduce body mass. In some other embodiments, the subject exhibits one or more symptoms consistent with poor glycemic control, such as an a higher percentage of time outside of target blood-glucose range (e.g., in a hypoglycemic range or in a hyperglycemic range). In some such embodiments, administering the liver-selective GK activator in combination with insulin or an analog thereof is carried out to increase the percentage of time in target blood-glucose range, decrease the percentage of time in hyperglycemic range, decrease the percentage of time in hypoglycemic range, or reduce number of hypoglycemic or severe hypoglycemic events over a period of time. Thus, in some such embodiments, administering the liver-selective glucokinase activator in combination with insulin or an analog thereof is carried out to reduce the bolus insulin dose or doses, the bolus insulin dose at each meal, the basal insulin dose or doses, or total insulin dose over a period of time. In some embodiments, the subject exhibits elevated mean daily blood-glucose levels. Thus, in some such embodiments, administering the liver-selective glucokinase activator in combination with insulin or an analog thereof is carried out to reduce mean daily blood-glucose levels. In some embodiments, the subject experiences an increased risk of diabetic ketoacidosis. Thus, in some embodiments, administering the liver-selective glucokinase activator in combination with insulin or an analog thereof is carried out to reduce the incidence, duration, or likelihood of ketoacidosis.

Doses of GK Activator

Any suitable dose and dosing schedule of the liver-selective GK activator can be used. In some embodiments, the methods disclosed herein comprise administering from 1 to 30 mg/kg daily of the liver-selective GK activator. These quantities may be administered in any suitable regimen throughout the day. In some embodiments, the administering comprises administering the liver-selective GK activator one or more times a day, such as one time a day, two times a day, three times a day, and the like. In some further such embodiments, the administering comprises administering the liver-selective GK activator two times a day. The administering may occur with or without food. In some embodiments wherein the administering comprises administering the liver-selective GK activator one or more times a day, at least one of the one or more times is with food. In some such embodiments, the administering comprises administering the liver-selective GK activator two times a day with food. In some embodiments, the two or more daily doses contain equal amounts of the liver-selective GK activator. In other embodiments, the methods include administering from 1 to 30 mg/kg every other day of the liver-selective GK activator, or every third day, or every fourth day, or every fifth day, every sixth day. A single administered dosage form may comprise between 1-75 mg, 75-100 mg, 75-150 mg, 100-150 mg, 125-175 mg, 150-200 mg, 175-225 mg, 200-250 mg, 225-275 mg, 250-300 mg, 275-325 mg, 300-350 mg, 325-375 mg, 350-400 mg, 375-425 mg, 400-450 mg, 425-475 mg, 450-500 mg, 475-525 mg, 500-550 mg, 525-575 mg, 550-600 mg, 575-625 mg, 600-650 mg, 625-675 mg, 675-725 mg, 700-750 mg, 725-800 mg, or 775-825 mg of liver-selective GK activator. In other embodiments, a liver-selective is administered in one or more doses to a subject in an amount that ranges from 100 mg/day to 2000 mg/day, or from 200 mg/day to 1500 mg/day, or from 400 mg/day to 1200 mg/day, or from 500 mg/day to 1200 mg/day, or from 800 mg/day to 1200 mg/day.

The duration of the methods disclosed herein may be carried out over any suitable period of time, depending on treatment goals. Because type 1 diabetes and its related disorders are chronic conditions, the administering may, in some embodiments, be carried out indefinitely, such as for several years or more. In some embodiments, the administering comprises administering the liver-selective GK activator for a period of time no less than one week, or no less than two weeks, or no less than three weeks, or no less than six weeks, or no less than nine weeks, or no less than twelve weeks.

Administration of the insulin or analog thereof can be carried out using any suitable method. For example, in some embodiments, the insulin or analog thereof is administered in conjunction with continuous glucose monitoring, such that the insulin or analog thereof is administered as needed depending on glucose levels.

Other Antidiabetic Agents

In some embodiments of any of the foregoing aspects and embodiments, the liver-selective GK activator and insulin or analog thereof can also be co-administered with one or more other antidiabetic agents. In this context, the terms "coadministering" does not necessarily imply that the antidiabetic agents are administered on the same schedule as the liver-selective GK activator or insulin or analog thereof. After all, in some instances, these medications may be once-daily or once-weekly medications. Thus, in this context, the term "coadministering" refers to administering the drugs in such a way that the one or more other antidiabetic agents have a non-zero concentration in the blood of the subject at the time of administering the liver-selective GK activator. In some embodiments, the liver-selective GK activator and one or more antidiabetic agents are formulated into the same dosage form, such as a tablet or capsule for oral administration. In other embodiments, they are formulated separately, and administered in a suitable means for the respective dosage forms.

Any suitable antidiabetic agents can be used. For example, in some embodiments, the one or more antidiabetic agents are selected from the group consisting of: biguanides (including metformin, phenformin, and buformin), thiazolidinediones (including rosiglitazone, pioglitazone, and troglitazone), sulfonylureas (including tolbutamide, acetohexamide, tolazamide, chlorpropamide, glipizide, glibenclamide, glimepiride, gliclazide, glyclopyramide, and gliquidone), meglitinides (including repaglinide and nateglinide), alpha-glucosidase inhibitors (including miglitol, acarbose, and voglibose), glucagon-like peptide analogs and agonists (including exenatide, liraglutide, semaglutide, taspoglutide, lixisenatide, albuglutide, and dulaglutide), gastric inhibitory peptide analogs, dipeptidyl peptidase-4 (DPP-4) inhibitors (including vildagliptin, sitagliptin, saxagliptin, linagliptin, alogliptin, septagliptin, teneligliptin, and gemigliptin), amylin agonist analogs, sodium/glucose cotransporter inhibitors (such as dual SGLT1 and SGLT2 inhibitors or selective SGLT2 inhibitors), and glucagon-like peptide (GLP) analogs and agonists. In some such embodiments, the one or more antidiabetic agents is metformin. In another such embodiment, the one or more antidiabetic agents is a sodium/glucose cotransporter inhibitor such as sotagliflozin, empagliflozin, dapagliflozin, canagliflozin, or ertugliflozin.

In embodiments where metformin is coadministered in combination with the liver-selective GK activator, the coadministering comprises orally coadministering from 1 to 30 mg/kg daily of metformin to the subject or coadministering between 1 mg to 2,500 mg daily of metformin to the subject. This coadministering can occur in any suitable dosages. In some embodiments, the coadministering comprises coadministering metformin one or more times a day, such as one time a day, two times a day, three times a day, four times a day, and the like. In some such embodiments, the coadministering comprises coadministering metformin two times a day. In some further such embodiments, the coadministering comprises coadministering metformin two times a day with food. In some embodiments, the two or more daily doses contain equal amounts of metformin. In some further embodiments of any of the foregoing aspects and embodiments, coadministering metformin comprises administering to a subject in need thereof from 1 to 25 mg/kg daily of metformin. In some other such embodiments, coadministering metformin comprises coadministering to a human subject in need thereof from 100 to 2000 mg daily of metformin.

In some other such embodiments where an SGLT inhibitor is coadministered with the liver-selective GK activator, the coadministration comprises orally administering a daily dose of an SGLT inhibitor at or below the daily dose provided on the related product insert for the SGLT inhibitor.

Uses for Lowering Glycated Hemoglobin

The foregoing methods are set forth as general methods. In some embodiments of any of the foregoing aspects and embodiments, the methods are methods of lowering glycated hemoglobin levels in a subject. In some further such embodiments, lowering glycated hemoglobin levels comprises lowering HbA1c levels in a subject. For example, in some embodiments, lowering glycated hemoglobin levels comprises lowering HbA1c levels in a subject by an absolute amount of at least 0.1%, of at least 0.3%, or an absolute amount of at least 0.5%, or an absolute amount of at least 0.7%, or an absolute amount of at least 0.9%, or an absolute amount of at least 1.0%, where HbA1c levels are measured as a percentage according to the National Glycohemoglobin Standardization Program (NGSP) protocol.

In some other embodiments of any of the foregoing aspects and embodiments, the disclosure provides uses of liver-selective GK activators in combination with insulin or analogs thereof for use in lowering elevated glycated hemoglobin levels in a subject according to any of the embodiments set forth above. In some other embodiments of any of the foregoing aspects and embodiments, the disclosure provides uses of liver-selective GK activators in the manufacture of a medicament for use in combination with insulin or analogs thereof for lowering elevated levels of glycated hemoglobin in a subject, wherein the medicament is prepared to be administered to a subject according to any of the methods set forth above.

In other embodiments herein, achievement of measures of improved glycemic control may be achieved without any reduction in HbA1c levels or even with an increase in HbA1c levels.

Uses for Treating Diabetes

The foregoing methods are set forth as general methods. In some embodiments of any of the foregoing aspects and embodiments, the methods are methods of treating type 1 diabetes. In other embodiments of any of the foregoing aspects and embodiments, the methods are methods of treating type 2 diabetes in a subject that is using insulin with or without another antidiabetic agent to regulate blood glucose levels.

In some other embodiments of any of the foregoing aspects and embodiments, the disclosure provides uses of liver-selective GK activators in combination with insulin or analogs thereof for treating type 1 diabetes according to any of the embodiments set forth above. In some other embodiments of any of the foregoing aspects and embodiments, the disclosure provides uses of liver-selective GK activators in the manufacture of a medicament for use in combination with insulin or analogs thereof for treating type 1 diabetes, wherein the medicament is prepared to be administered to a subject according to any of the methods set forth above.

In some other embodiments of any of the foregoing aspects and embodiments, the disclosure provides uses of liver-selective GK activators in combination with insulin or analogs thereof for treating type 2 diabetes in a subject that is also using insulin to regulate blood glucose levels with or without another antidiabetic agent according to any of the embodiments set forth above. In some other embodiments of any of the foregoing aspects and embodiments, the disclosure provides uses of liver-selective GK activators in the manufacture of a medicament for use in combination with insulin or analogs thereof for treating type 2 diabetes in a subject that is also using insulin to regulate blood glucose levels with or without another antidiabetic agent, wherein the medicament is prepared to be administered to a subject according to any of the methods set forth above.

Uses for Reducing Body Mass

The foregoing methods are set forth as general methods. In some embodiments of any of the foregoing aspects and embodiments, the methods are methods of reducing body mass. In some further such embodiments, the methods comprise reducing body-mass index (BMI) of a subject having elevated BMI levels by an absolute amount of at least 0.5, or at least 1.0, or at least 1.5, or at least 2.0. In other embodiments, the subject's body weight may be reduced by at least 0.1, or 0.2, or 0.3, or 0.4, or 0.5, or 0.6, or, 0.7, or 0.8, or 0.9, or 1.0, or 1.5, or 2.0 kg. In another embodiment, the subject's BMI or body weight is reduced over a period of 1, 2, 3, 4, 5, 6, 7, or 8 week(s), or 3, 4, 5 or 6 months.

In some other embodiments of any of the foregoing aspects and embodiments, the disclosure provides uses of liver-selective GK activators in combination with insulin or analogs thereof in reducing body mass according to any of the embodiments set forth above. In some other embodiments of any of the foregoing aspects and embodiments, the disclosure provides uses of liver-selective GK activators in the manufacture of a medicament for use in combination with insulin or analogs thereof for reducing body mass, wherein the medicament is prepared to be administered to a subject according to any of the methods set forth above.

Uses for Improving Glycemic Control

The foregoing methods are set forth as general methods. In some embodiments of any of the foregoing aspects and embodiments, the methods are methods of improving glycemic control.

In some embodiments, the methods are methods of increasing the percentage of time in target blood-glucose range, i.e., for humans, within a range of from 70 mg/dL to 180 mg/dL per unit time. In some such embodiments, the methods comprise increasing the percentage time in target blood-glucose range by an absolute percentage of at least 1%, at least 2%, at least 3%, at least 4%, at least 5%, at least 6%, or at least 8%, or at least 10%, or at least 12%, or at least 14%, based on the absolute difference of percentage of time in target blood-glucose range for a period of time relative to baseline (such as administering only insulin or an analog thereof).

In other embodiments, the methods are methods of increasing percentage of time between meals (such as 2 hours after previous meal and immediately before next meal) in blood glucose range of 80-130 mg/dL. (Pre-prandial range). In other embodiments, the methods are methods of increasing percentage of time after beginning of meal and ending 2 hours after meal in blood glucose level of less than or equal to 180 mg/dL. The percentage of increase of time in these methods may be an absolute percentage of at least 1%, at least 2%, at least 3%, at least 4%, at least 5%, at least 6%, or at least 8%, or at least 10%, or at least 12%, or at least 14%, based on the difference of percentage of time in target blood-glucose range relative to baseline (such as administering only insulin or an analog thereof).

In some embodiments, the methods are methods of decreasing the percentage of time in hypoglycemic range or severe hypoglycemic range. In some such embodiments, the methods comprise decreasing the percentage time in hypoglycemic range or severe hypoglycemic range by an absolute percentage of at least 1%, at least 2%, at least 3%, at least 4%, at least 5%, at least 6%, or at least 8%, or at least 10%, or at least 12%, or at least 14%, based on the absolute difference of percentage of time in target blood-glucose range for a period of time relative to baseline (such as administering only insulin or an analog thereof).

In some embodiments, the methods are methods of decreasing the percentage of time in hyperglycemic range or severe hyperglycemic range. In some such embodiments, the methods comprise decreasing the percentage time in hyperglycemic range or severe hyperglycemic range by an absolute percentage of at least 1%, at least 2%, at least 3%, at least 4%, at least 5%, at least 6%, or at least 8%, or at least 10%, or at least 12%, or at least 14%, based on the absolute difference of percentage of time in target blood-glucose range relative to baselines (such as administering only insulin or an analog thereof).

In some embodiments, the methods are methods of reducing the number of hypoglycemic events or severe hypoglycemic events over a period of time. In some such embodiments where the subject is using CGM, the methods comprise reducing the number of hypoglycemic events or severe hypoglycemic events over a period of time by an absolute amount of at least 1 event or 2 events. In other such embodiments where the subject is using SMBG, the methods comprise reducing the number of hypoglycemic events or severe hypoglycemic events over a period of time by an absolute amount of at least 1 event, 2 events, 10 events, 20 events, 30 events, 50 events, 70 events. In some embodiments, the period of time may be 1 day, 2 days, 3 days, 4 days, 5 days, 6 days, or 7 days.

In other embodiments, the methods comprise reducing the number of hyperglycemic events or severe hyperglycemic events over a period of time. In some such embodiments where the subject is using CGM, the methods comprise reducing the number of hyperglycemic events or severe hyperglycemic events over a period of time by an absolute amount of at least 1 event or 2 events. In other such embodiments where the subject is using SMBG, the methods comprise reducing the number of hyperglycemic events or severe hyperglycemic events over a period of time by an absolute amount of at least 1 event, 2 events, 10 events, 20 events, 30 events, 50 events, 70 events. In some embodiments, the period of time is 1 day, or 2 days, 3 days, 4 days, 5 days, 6 days, or 7 days.

In some other embodiments of any of the foregoing aspects and embodiments, the disclosure provides uses of liver-selective GK activators in combination with insulin or analogs thereof in increasing the percentage of time in target blood-glucose range, decreasing the percentage of time in hypoglycemic range, decreasing the percentage of time in hyperglycemic range, decreasing the time in severe hypoglycemic range, reducing the number of hyperglycemic events, or reducing the number of severe hypoglycemic events, according to any of the embodiments set forth above. In some other embodiments of any of the foregoing aspects and embodiments, the disclosure provides uses of liver-selective GK activators in the manufacture of a medicament for use in combination with insulin or analogs thereof in increasing the percentage of time in target blood-glucose range, decreasing the percentage of time in hypoglycemic range, decreasing the percentage of time in hyperglycemic range, decreasing the time in severe hypoglycemic range, reducing the number of hyperglycemic events, or reducing the number of severe hypoglycemic events wherein the medicament is prepared to be administered to a subject according to any of the methods set forth above.

Uses for Lowering Insulin Dose

The foregoing methods are set forth as general methods. In some embodiments of any of the foregoing aspects and embodiments, the methods are methods of reducing insulin (or analog thereof) doses for a subject for example on a per dose basis, per day basis, or per week basis, or other period. In some further such embodiments, the methods comprise reducing insulin (or analog thereof) dose by at least 1%, at least 2%, at least 3%, at least 4%, at least 5%, at least 7%, at least 10%, at least 15%, at least 20%, or at least 25%, or by an absolute amount of at least 1 unit, 2 units, 3 units, 4 units, 5 units, 6 units, 7 units, 8 units, 9 units, or 10 units based on the baseline insulin (or analog thereof) dose (such as treatment only with insulin or an analog thereof).

Uses for Reducing Total Daily Bolus Insulin Dose

In some embodiments, the methods are methods of reducing the total daily bolus insulin dose. In some such embodiments, the methods comprise reducing total daily bolus insulin (or analog thereof) dose by at least 1%, at least 2%, at least 3%, at least 4%, at least 5%, at least 7%, at least 10%, at least 15%, at least 20%, or at least 25%, or by an absolute amount of at least 1 unit, 2 units, 3 units, 4 units, 5 units, 6 units, 7 units, 8 units, 9 units, or 10 units based on the baseline total daily bolus insulin (or analog thereof) dose (such as treatment only with insulin or an analog thereof).

Uses for Reducing Total Daily Basal Insulin Dose

In some embodiments, the methods are methods of reducing the total daily basal insulin dose. In some such embodiments, the methods comprise reducing total daily basal insulin (or analog thereof) dose by at least 1%, at least 2%, at least 3%, at least 4%, at least 5%, at least 7%, at least 10%, at least 15%, at least 20%, or at least 25%, or by an absolute amount of at least 1 unit, 2 units, 3 units, 4 units, 5 units, 6 units, 7 units, 8 units, 9 units, or 10 units based on the baseline total daily basal insulin (or analog thereof) dose (such as treatment only with insulin or an analog thereof).

Uses for Reducing Total Daily Insulin Dose

In some embodiments, the methods are methods of reducing the total daily insulin dose. In some such embodiments, the methods comprise reducing total daily insulin (or analog thereof) dose by at least 1%, at least 2%, at least 3%, at least 4%, at least 5%, at least 7%, at least 10%, at least 15%, at least 20%, or at least 25%, or by an absolute amount of at least 1 unit, 2 units, 3 units, 4 units, 5 units, 6 units, 7 units, 8 units, 9 units, or 10 units based on the baseline total daily insulin (or analog thereof) dose (such as treatment only with insulin or an analog thereof).

Uses for Reducing the Number or Doses of Insulin Injections

In some embodiments, the methods are methods of reducing the number of insulin injections over a period of time, where the period of time may be 1 days, 1 week, or 1 month. In some embodiment, the total number of insulin injections may be reduced by 1, 2, 3, or more. In other embodiments, the methods are methods of reducing the number of daily basal insulin injections, where the number of injections may be reduced by 1, 2, 3, or more. In other embodiments, the methods are methods of reducing the number of daily bolus insulin injections, where the number of injections may be reduced by 1, 2, 3, or more. In another embodiment, the number of insulin injections per day are no more than 1 or 2 or 3.

In some other embodiments of any of the foregoing aspects and embodiments, the disclosure provides uses of liver-selective GK activators in combination with insulin or analogs thereof in lowering insulin doses or injection according to any of the embodiments set forth above. In some other embodiments of any of the foregoing aspects and embodiments, the disclosure provides uses of liver-selective GK activators in the manufacture of a medicament for use in combination with insulin or analogs thereof for lowering insulin doses or injections, wherein the medicament is prepared to be administered to a subject according to any of the methods set forth above.

Uses for Lowering Mean Daily Blood-Glucose

The foregoing methods are set forth as general methods. In some embodiments of any of the foregoing aspects and embodiments, the methods are methods of reducing mean daily blood-glucose levels. In some further such embodiments, the methods comprise reducing mean daily blood-glucose levels by at least 5 mg/dL, or at least 7 mg/dL, or at least 10 mg/dL, or at least 15 mg/dL, or at least 20 mg/dL, or at least 25 mg/dL, or at least 30 mg/dL, or at least 35 mg/dL relative to baseline treatment (such as using only insulin or an analog thereof).

In some other embodiments of any of the foregoing aspects and embodiments, the disclosure provides uses of liver-selective GK activators in combination with insulin or analogs thereof in lowering mean daily blood-glucose levels according to any of the embodiments set forth above. In some other embodiments of any of the foregoing aspects and embodiments, the disclosure provides uses of liver-selective GK activators in the manufacture of a medicament for use in combination with insulin or analogs thereof for lowering mean daily blood-glucose levels, wherein the medicament is prepared to be administered to a subject according to any of the methods set forth above.

Uses for Lowering Glucagon Levels

Glucagon is a polypeptide hormone that is produced by the alpha cells of the pancreas. It is a hyperglycemic agent that mobilizes glucose by activating hepatic glycogenolysis (the breakdown of glycogen especially into glucose). However, excess levels of glucagon may lead to temporary changes in blood pressure, increased heart rate, nausea, vomiting, and/or hyperglycemia and certain antidiabetic drugs, such as SGLT2 inhibitors, may trigger excessive glucagon secretion.

The foregoing methods are set forth as general methods. In some embodiments of any of the foregoing aspects and embodiments, the methods are methods of reducing plasma glucagon levels and/or not increasing plasma glucagon levels. In some further such embodiments, the methods comprise reducing glucagon levels by at least 5 pg/mL, or at least 10 pg/mL, or at least 25 pg/mL, or at least 30 pg/mL, or at least 35 pg/mL, or at least 50 pg/mL, or at least 75 pg/mL relative to baseline treatment (such as using only insulin or an analog thereof) or reducing glucagon levels below 200 pg/mL, or below 150 pg/mL, or below 100 pg/mL.

In some other embodiments of any of the foregoing aspects and embodiments, the disclosure provides uses of liver-selective GK activators in combination with insulin or analogs thereof in lowering plasma glucagon levels according to any of the embodiments set forth above. In some other embodiments of any of the foregoing aspects and embodiments, the disclosure provides uses of liver-selective GK activators in the manufacture of a medicament for use in combination with insulin or analogs thereof for lowering plasma glucagon levels, wherein the medicament is prepared to be administered to a subject according to any of the methods set forth above.

Uses for Reducing Incidence, Duration, or Likelihood of Diabetic Ketoacidosis

The foregoing methods are set forth as general methods. In some embodiments of any of the foregoing aspects and embodiments, the methods are methods of reducing the incidence, duration, or likelihood of diabetic ketoacidosis. In an embodiment, diabetic ketoacidosis is defined as a subject having elevated level of one or more metabolic ketones such as serum or urine ketones (greater than upper limit of normal range), and having a blood pH of 7.3 or less and a serum bicarbonate level of 18 mmol/L or less. In another embodiment, diabetic ketoacidosis is defined as a subject having elevated plasma, serum or urine ketones (greater than upper limit of normal range), or having a blood pH of less than 7.3 or a serum bicarbonate level of 18 mmol/L or less, or 15 mmol/L or less or the equivalent measure in mEq/L, or blood glucose level of greater than 250 mg/dL, or a combination of any of the foregoing measures. In an embodiment, the metabolic ketone is selected from the group consisting of acetoacetate (AcAc), beta-hydroxybutyrate (BHB), and acetone. In a further embodiment, the level of AcAc is measured in the subject's serum. In another embodiment, the level of BHB is measured in the subject's urine. In another embodiment, the level of BHB is measured in the subject's blood. In a further embodiment, the level of one or more of metabolic ketones is between 0.3 and 0.5 mM, or greater than 0.5 mM, or between 0.5 and 1.0 mM, or between 1.0 and 3.0 mM, or greater than 3.0 mM, or 4.0 mM, or 5.0 mM, 10 mM, or 15 mM, or 20 mM. In some further such embodiments, the methods comprise reducing the incidence of diabetic ketoacidosis by at least 5%, or at least 10%, or at least 15%, relative to baseline treatment (such as using only insulin or an analog thereof), over a relevant period of time, such as one week, one month, two months, three months, etc.

In some other embodiments of any of the foregoing aspects and embodiments, the disclosure provides uses of liver-selective GK activators in combination with insulin or analogs thereof in reducing the incidence, duration, or likelihood of diabetic ketoacidosis according to any of the embodiments set forth above. In some other embodiments of any of the foregoing aspects and embodiments, the disclosure provides uses of liver-selective GK activators in the manufacture of a medicament for use in combination with insulin or analogs thereof for reducing the incidence, duration, or likelihood of diabetic ketoacidosis, wherein the medicament is prepared to be administered to a subject according to any of the methods set forth above.

Uses for Reducing Incidence, Duration, or Likelihood of Diabetic Ketosis

The foregoing methods are set forth as general methods. In some embodiments of any of the foregoing aspects and embodiments, the methods are methods of reducing the incidence, duration, or likelihood of diabetic ketosis. In an embodiment, diabetic ketosis is defined as a subject having elevated metabolic ketones such as serum or urine ketones (greater than upper limit of normal range), and while having blood sugar and or blood pH in normal range. For example, diabetic ketosis may occur when a subject's blood pH is equal to or above pH of 7.3 and/or has a serum bicarbonate level of greater than 15 mmol/L, 18 mmol/L, or 20 mmol/L. In further embodiments, subject's blood glucose level is less than 250 mg/dL or less than 200 mg/dL, or less than 180 mg/dL. In an embodiment, the metabolic ketone indicating an incidence of diabetic ketosis is selected from the group consisting of acetoacetate (AcAc), beta-hydroxybutyrate (BHB), and acetone. In a further embodiment, the level of AcAc is measured in the subject's blood or urine. In another embodiment, the level of BHB is measured in a sample taken from the subject's blood or urine. In another embodiment, the level of acetone is measured in a sample of the subject's breath. In a further embodiment, the level of one or more of metabolic ketones indicating diabetic ketosis is between 0.3 and 0.5 mM, or greater than 0.5 mM, or between 0.5 and 1.0 mM, or between 1.0 and 3.0 mM, or between 3.0 mM and 6.0 mM, or between 6.0 mM and 10 mM, or greater than 5 mM or 10 mM or 15 mM or 20 mM or 25 mM. In some further such embodiments, the methods comprise reducing the incidence of diabetic ketosis by at least 5%, or at least 10%, or at least 15%, relative to baseline treatment (such as using only insulin or an analog thereof), over a relevant period of time, such as one week, one month, two months, three months, etc. In some other embodiments of any of the foregoing aspects and embodiments, the disclosure provides uses of liver-selective GK activators in combination with insulin or analogs thereof in reducing the incidence, duration, or likelihood of diabetic ketosis according to any of the embodiments set forth above. In some other embodiments of any of the foregoing aspects and embodiments, the disclosure provides uses of liver-selective GK activators in the manufacture of a medicament for use in combination with insulin or analogs thereof for reducing the incidence, duration, or likelihood of diabetic ketoacidosis, wherein the medicament is prepared to be administered to a subject according to any of the methods set forth above.

Uses for Reducing Metabolic Ketones

The foregoing methods are set forth as general methods. In some embodiments of any of the foregoing aspects and embodiments, the methods are methods of reducing the level of metabolic ketones in a subject. In an embodiment, the metabolic ketones reduced are selected from the group consisting of acetoacetate (AcAc), beta-hydroxybutyrate (BHB), and acetone. In a further embodiment, the level of AcAc is reduced. In another embodiment, the level of BHB is reduced. In another embodiment, the level of one or more metabolic ketone(s) is reduced by at least 0.1 mM, 0.2 mM, 0.3 mM, 0.4 mM, 0.5 mM, 0.6 mM, 0.7 mM, 0.8 mM, or 0.9 mM, or reduced by at least 1%, 2%, 3%, 4%, 5%, 10%, 15%, 20%, 30%, 35%, 40%, 45%, or 50% relative to a baseline measurement, such as before treatment. In another embodiment, the level of BHB is reduced by at least 0.1 mM, 0.2 mM, 0.3 mM, 0.4 mM, 0.5 mM, 0.6 mM, 0.7 mM, 0.8 mM, or 0.9 mM, or reduced by at least 1%, 2%, 3%, 4%, 5%, 10%, 15%, 20%, 30%, 35%, 40%, 45%, or 50% relative to a baseline measurement, such as before treatment. In another embodiment, the level of AcAc is reduced by at least 0.1 mM, 0.2 mM, 0.3 mM, 0.4 mM, 0.5 mM, 0.6 mM, 0.7 mM, 0.8 mM, or 0.9 mM, or reduced by at least 1%, 2%, 3%, 4%, 5%, 10%, 15%, 20%, 30%, 35%, 40%, 45%, or 50% relative to a baseline measurement, such as before treatment. In another embodiment, the level of acetone is reduced by at least 0.1 mM, 0.2 mM, 0.3 mM, 0.4 mM, 0.5 mM, 0.6 mM, 0.7 mM, 0.8 mM, or 0.9 mM, or reduced by at least 1%, 2%, 3%, 4%, 5%, 10%, 15%, 20%, 30%, 35%, 40%, 45%, or 50% relative to a baseline measurement, such as before treatment. In some further such embodiments, the methods comprise reducing the level of one or more metabolic ketones relative to baseline treatment (such as using only insulin or an analog thereof), over a relevant period of time, such as one week, one month, two months, three months, etc.

In some other embodiments of any of the foregoing aspects and embodiments, the disclosure provides uses of liver-selective GK activators in combination with insulin or analogs thereof in reducing the level of metabolic ketones according to any of the embodiments set forth above. In some other embodiments of any of the foregoing aspects and embodiments, the disclosure provides uses of liver-selective GK activators in the manufacture of a medicament for use in combination with insulin or analogs thereof for reducing the level of metabolic ketones, wherein the medicament is prepared to be administered to a subject according to any of the methods set forth above.

Uses for Reducing Incidence, Duration, or Likelihood of Diabetic Lactic Acidosis The foregoing methods are set forth as general methods. In some embodiments of any of the foregoing aspects and embodiments, the methods are methods of reducing the incidence, duration, or likelihood of diabetic lactic acidosis. In an embodiment, diabetic lactic acidosis is defined as a subject having an elevated level of lactic acid such as above 1.0 mM, 1.5 mM, 2.0 mM, 2.5 mM, 3.0 mM, 3.5 mM, 4.0 mM, 4.5 mM, 5.0 mM, 10 mM, or 15 mM. In another embodiment, diabetic lactic acidosis is defined as a subject having elevated arterial blood lactate concentration (such as above 14.4 mg/dL or 1.6 mM) or venous blood lactate concentration (such as above 19.8 mg/dL or 2.2 mM), or an equivalent concentration of lactate concentration in capillary blood. In some further such embodiments, the methods comprise reducing the incidence of diabetic lactic acidosis by at least 5%, or at least 10%, or at least 15%, relative to baseline treatment (such as using only insulin or an analog thereof), over a relevant period of time, such as one week, one month, two months, three months, etc.

In some other embodiments of any of the foregoing aspects and embodiments, the disclosure provides uses of liver-selective GK activators in combination with insulin or analogs thereof in reducing the incidence, duration, or likelihood of diabetic lactic acidosis according to any of the embodiments set forth above. In some other embodiments of any of the foregoing aspects and embodiments, the disclosure provides uses of liver-selective GK activators in the manufacture of a medicament for use in combination with insulin or analogs thereof for reducing the incidence, duration, or likelihood of diabetic lactic acidosis, wherein the medicament is prepared to be administered to a subject according to any of the methods set forth above.

Uses for Reducing Lactate

The foregoing methods are set forth as general methods. In some embodiments of any of the foregoing aspects and embodiments, the methods are methods of reducing the level of lactate in a subject. In an embodiment, the level of lactate is reduced by at least 0.1 mM, 0.2 mM, 0.3 mM, 0.4 mM, 0.5 mM, 0.6 mM, 0.7 mM, 0.8 mM, 0.9 mM, 1.0 mM, 1.5 mM, 2.0 mM, or reduced by at least 1 mg/dL, or 2 mg/dL, or 3 mg/dL, or 4 mg/dL or 5 mg/dL or 10 mg/dL, or reduced to below 3.0 mM, or reduced to below 2.5 mM, or reduced to below 2.0 mM, or reduced to below 1.5 mM, or reduced to below 1.0 mM, or reduced by at least 1%, 2%, 3%, 4%, 5%, 10%, 15%, 20%, 30%, 35%, 40%, 45%, or 50% relative to a baseline measurement, such as before treatment. In another embodiment, the level of lactate is measured in the arterial blood. In another embodiment, the level of lactate is measured in venous blood. In some further such embodiments, the methods comprise reducing the level of lactate relative to baseline treatment (such as using only insulin or an analog thereof), over a relevant period of time, such as one week, one month, two months, three months, etc.

In some other embodiments of any of the foregoing aspects and embodiments, the disclosure provides uses of liver-selective GK activators in combination with insulin or analogs thereof in reducing the level of lactate according to any of the embodiments set forth above. In some other embodiments of any of the foregoing aspects and embodiments, the disclosure provides uses of liver-selective GK activators in the manufacture of a medicament for use in combination with insulin or analogs thereof for reducing the level of lactate, wherein the medicament is prepared to be administered to a subject according to any of the methods set forth above.

Assays

The methods of treatment disclosed herein can include a step of measuring one or more biomarkers before, during and/or after certain periods of treatment. In an embodiment, the method may further comprise obtaining or having obtained a biological sample or samples over a period of time from the subject and performing or having performed a bodily fluid test on the biological samples. The bodily fluid tests may be used to determine the percentage of time in a target blood-glucose range, the level of glycated hemoglobin, the percentage of time in hypoglycemic range, the percentage of time in hyperglycemic range, the incidence of or number incidences of diabetic ketoacidosis, the incidence of or number incidences of diabetic ketosis, the number of hypoglycemic or severe hypoglycemic events over a period of time, the number of hyperglycemic or severe hypoglycemic events over a period of time.

The biological sample or bodily fluid to be tested may includes fluids produced by the body, such as saliva, or fractions thereof, mucous secretions, tears, sweat, bile, semen, urine, vaginal secretions, exhalations, anal secretions, blood, plasma, serum and mixtures of thereof. In an embodiment, the biological sample or bodily fluid may be saliva, a mucous secretion, tears, sweat, urine, exhalate, blood, or serum.

The biomarkers that may be measured in the biological sample or bodily fluid include glucose, metabolic ketone(s), glucagon, glycosylated hemoglobin, lactate, and pH. In some embodiments, the method may comprise measuring a subject's blood glucose level, blood serum pH level, or serum bicarbonate level, one or more metabolic ketone(s) in a subject's blood, breath, or urine, measuring the level of glucagon hormone in a subject's blood, the level of lactate in a subjects blood, and/or measuring the level of glycated hemoglobin in the subject's blood, for example, levels of HbA1c in a subject's blood.

Biomarkers may be measured by any method known in the art. For example, glucose may be measured by using a continuous glucose monitoring device or glucose test strips. Blood pH may be measured by pH test strips, a calibrated pH meter. Glucagon may be measured by a radioimmunoassay or an ELISA assay. Urine ketone concentrations may be measured using over-the-counter reagent strips which determine the presence of AcAc upon reaction with nitroprusside salt. Blood ketone concentrations may be measured using an electrochemical capillary blood monitor device with the corresponding individually foil-wrapped test strips for BHB. Glycosylated hemoglobin may be measured using high-performance liquid chromatography, an immunoassay, an enzymatic assay, capillary electrophoresis, or boronate affinity chromatography. Lactate may be measured using a blood gas analyzer. Lactate may be measured by a portable/point of care analyzer such as those using enzymatic (lactic oxidase) amperometric detection methods, or may be measured by a device using an electrical amperometric metabolite sensor or ion selective electrode.

In another embodiment, the method may comprise the step of selecting a subject for treatment. In some embodiments, the subject is selected for treatment by determining whether a subject is at risk of developing diabetic ketoacidosis by measuring the level of a subject's blood glucose, blood pH, serum pH, serum bicarbonate, and/or one or more metabolic ketone(s) in a subject's. A subject may be at risk of developing diabetic ketoacidosis if the subject is determined to suffer from diabetic ketosis for example by having elevated levels of one or more metabolic ketones while not having abnormal blood sugar level and/or blood pH below 7.3. In embodiment, if a subject is determined to be at risk for developing diabetic ketoacidosis, the method further comprises administering to the subject a liver-selective glucokinase activator in combination with insulin or an analog thereof.

In other embodiments, the subject may be selected for treatment when the subject is in need of therapeutic lowering of metabolic ketone levels, therapeutic lowering of glucagon levels, therapeutic lowering of lactate levels, therapeutic lowering of blood sugar levels, therapeutic lowering of HbA1c levels, or therapeutic elevating of plasma pH levels. Thus, the method may first include the step of identifying whether a subject is in need of therapeutic lowering of metabolic ketone levels, therapeutic lowering of glucagon levels, therapeutic lowering of lactate levels, therapeutic lowering of blood sugar levels, therapeutic lowering of HbA1c levels, or therapeutic elevating of plasma pH levels. In an embodiment, the subject is identified for treatment after obtaining or having obtained a biological sample from the subject and performing or having performed a bodily fluid test on the biological sample to determine if the level of one or more biomarkers is associated with the need for a therapeutic modulation of its level.

In other embodiments, the subject may be selected for treatment when a combination of clinical symptoms, clinical events, and/or biomarker levels are identified. For example, a subject may be selected for treatment if the subject has had more than 1, 2, 3, 4, or 5 hyperglycemic events, severe hyperglycemic events, hypoglycemic events, or severe hypoglycemic events over a certain period. A subject may also be selected for treatment if the subject has elevated levels of one or more metabolic ketones, suffers from euglycemic ketoacidosis, has a blood pH at or below 7.3, has an HbA1c above 6.0, 6.5, 7.0, 7.5, 8.0, 8.5, or 9.0%, has elevated levels of lactate such as above 1.0 mM, or 2.0 mM, or 3.0 mM, or 4.0 mM and/or has a level of glucagon above 100 pg/mL, 130 pg/mL, 150 pg/mL, or 200 pg/mL or a combination of any of the foregoing. In any of the preceding methods, the method may further comprise obtaining or having obtained biological samples over a period of time from the subject and performing or having performed a bodily fluid test on the biological samples to determine whether the level of one or more biochemical markers are increasing or decreasing, and if the level of one or more biochemical markers are not trending in the desired direction then administering a greater dose of the liver-selective glucokinase activator.

Pharmaceutical Compositions Dosage Forms

The liver-selective GK activators can be formulated into any suitable pharmaceutical composition. As used herein, the term "pharmaceutical composition" refers to a composition (e.g., a granulated powder or a liquid) that contains a pharmaceutically active ingredient (e.g., a liver-selective GK activators) and a pharmaceutically acceptable carrier. As used herein, the term "pharmaceutically acceptable" refers to a substance that is not generally biologically undesirable at the administered quantities.

A single administered dosage form of a liver-selective GK activator may comprise between 1-75 mg, 75-100 mg, 75-150 mg, 100-150 mg, 125-175 mg, 150-200 mg, 175-225 mg, 200-250 mg, 225-275 mg, 250-300 mg, 275-325 mg, 300-350 mg, 325-375 mg, 350-400 mg, 375-425 mg, 400-450 mg, 425-475 mg, 450-500 mg, 475-525 mg, 500-550 mg, 525-575 mg, 550-600 mg, 575-625 mg, 600-650 mg, 625-675 mg, 675-725 mg, 700-750 mg, 725-800 mg, or 775-825 mg of the liver-selective GK activator.

In some embodiments, the liver-selective GK activators is included in separate pharmaceutical composition from any coadministered antidiabetic agents (such as metformin or an SGLT2 inhibitor), each of which also includes a pharmaceutically acceptable carrier. In other embodiments, the liver-selective GK activators is included in the same pharmaceutical composition with one or more coadministered antidiabetic agents (such as metformin or an SGLT2 inhibitor), which also includes a pharmaceutically acceptable carrier.

The pharmaceutical compositions, described herein, can be packaged in a form for oral administration as discrete units (i.e., dosage forms), such as capsules, tablets, sachets, or the like. Preparation of the solid compositions in forms intended for oral administration is within the ability of one skilled in the art, including the selection of pharmaceutically acceptable additional ingredients from the groups listed above in order to provide pharmaceutically elegant and palatable preparations. Such pharmaceutical compositions may be prepared by methods known in the pharmaceutical formulation art, for example, see Remington's Pharmaceutical Sciences, 18th Ed., (Mack Publishing Company, Easton, Pa., 1990).

EXAMPLES

Example 1—Study Design

An open-label, weekly dose escalation study with up to 3 dose escalations was conducted. Five adult patients with type 1 diabetes (T1DM) who were using a continuous glucose monitoring (CGM) device and insulin delivered by continuous subcutaneous insulin infusion (CSII) were dosed with a once daily with a dose of 400, 800 or 1200 mg of {2-[3-cyclohexyl-3-(trans-4-propoxy-cyclohexyl)-ureido]-thiazol-5-ylsulfanyl}-acetic acid (UT-1) for seven days at each dose level.

The initial 7 days (days −7 to −1) of the study were used to obtain baseline laboratory samples and to record baseline insulin doses and blood glucose levels during a patient's usual insulin, dietary, and activity regimen. The once daily treatment dose of UT-1 was administered morning meal. Safety labs were collected on days −7, 1, 8, 15, 21 and 28. Insulin pump data and CGM data for each dosing period was collected on days 1, 8, 15, 21, and 28. Insulin was adjusted by a patient as required to maintain glycemic control. Data from day 3 to day 6 of each dosing period or baseline period was used in the analysis of the data.

Results

No detrimental effect on liver function or plasma lipids was seen during the study. As shown in the data below and in the related figures, trends toward improved glycemic control while reducing insulin dose were also seen. Further trends toward improved glycemic control were seen in an increase in the ratio of mean carbohydrate intake per day to mean bolus insulin dose per day ratio from baseline to 400 mg dose, and from 400 mg dose to 800 mg dose. Pharmacokinetic data indicated that the 1200 mg group concentrations of UT-1 were lower in 3 out of 5 subjects when compared to the 800 mg group.

In FIG. 1, the median value of the percentage of time blood glucose levels were in the range of 70-180 mg/dL increased from baseline (52.0%) to the 400 mg dose (67.9%), and from the 400 mg dose (67.9%) to the 800 mg dose (75.7%). The data used to prepare FIG. 1 is provided in Table 1 below.

TABLE 1

Percentage of time (using CGM) blood glucose level is in range of 70-180 mg/dL for each at baseline and at each dose.

| | | Dose of UT-1 | | |
|---|---|---|---|---|
| Subject | Baseline (%) | 400 mg (%) | 800 mg (%) | 1200 mg (%) |
| 1 | 49.7 | 67.9 | 82.7 | 69.6 |
| 2 | 80.0 | 56.8 | 75.7 | 59.3 |
| 3 | 52.0 | 69.3 | 44.3 | 52.9 |
| 4 | 47.2 | 56.3 | 65.4 | 48.8 |
| 5 | 60.5 | 69.6 | 85.9 | 80.9 |

Each data point in Table 1 represents the median of four days (days 3-6) at each dose for each subject.

Figure 2:
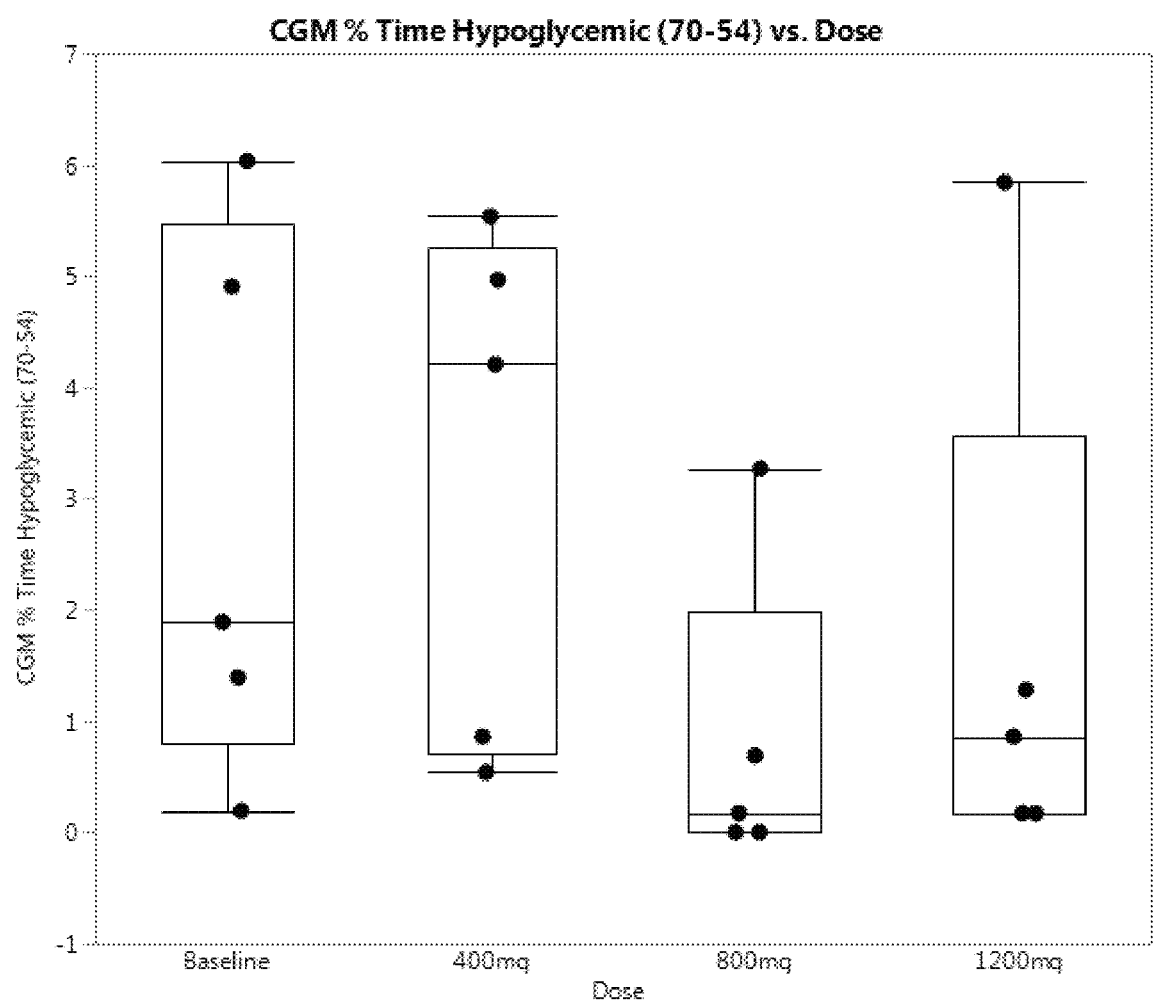
FIG. 2 displays the percentage of time each subject's blood glucose level was between 54 and 70 mg/dL at each dose (400, 800, and 1200 mg/day of UT-1) and for baseline, where each data point represents the median of four days (days 3-6) at each dose for each subject.

The data used to prepare FIG. 2 is provided in Table 2.

TABLE 2

Percentage of time (using CGM) blood glucose level is between 54 and 70 mg/dL for each subject at baseline and at each dose.

| | | Dose of UT-1 | | |
|---|---|---|---|---|
| Subject | Baseline (%) | 400 mg (%) | 800 mg (%) | 1200 mg (%) |
| 1 | 1.39 | 0.54 | 0.69 | 1.28 |
| 2 | 1.89 | 4.97 | 0 | 5.84 |
| 3 | 4.9 | 4.2 | 3.27 | 0.17 |
| 4 | 0.2 | 0.86 | 0 | 0.17 |
| 5 | 6.03 | 5.54 | 0.17 | 0.86 |

Each data point in Table 2 represents the median of four days (days 3-6) at each dose for each subject.

Figure 3:
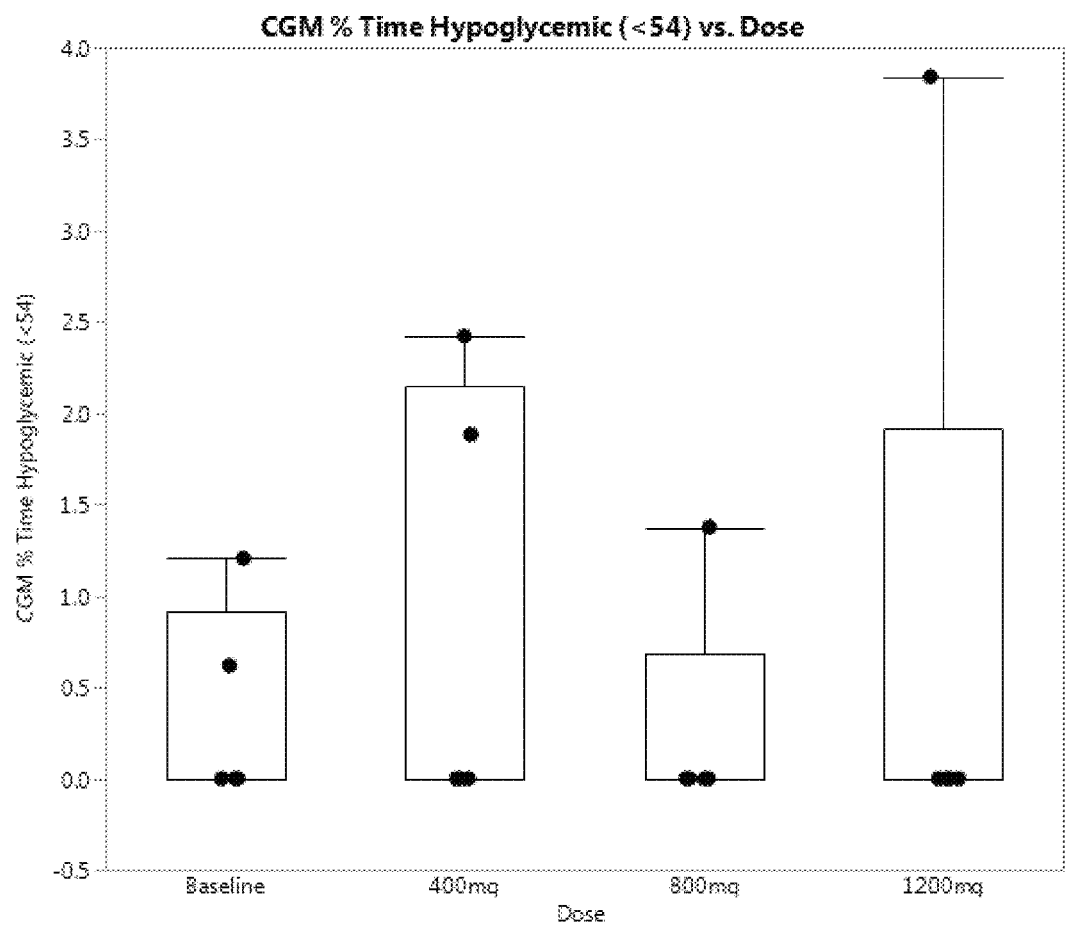
FIG. 3 displays the percentage of time each subject's blood glucose level was less than 54 mg/dL at each dose (400, 800, and 1200 mg/day of UT-1) and for baseline, where each data point represents the median of four days (days 3-6) at each dose for each subject.

The data used to prepare FIG. 3 is provided in Table 3.

TABLE 3

Percentage of time (using CGM) blood glucose level is below 54 mg/dL for each subject at baseline and at each dose.

| | | Dose of UT-1 | | |
|---|---|---|---|---|
| Subject | Baseline (%) | 400 mg (%) | 800 mg (%) | 1200 mg (%) |
| 1 | 0 | 0 | 0 | 0 |
| 2 | 0 | 1.88 | 0 | 3.84 |
| 3 | 0.62 | 0 | 1.38 | 0 |
| 4 | 0 | 0 | 0 | 0 |
| 5 | 1.21 | 2.42 | 0 | 0 |

Each data point in Table 3 represents the median of four days (days 3-6) at each dose for each subject.

Figure 4:
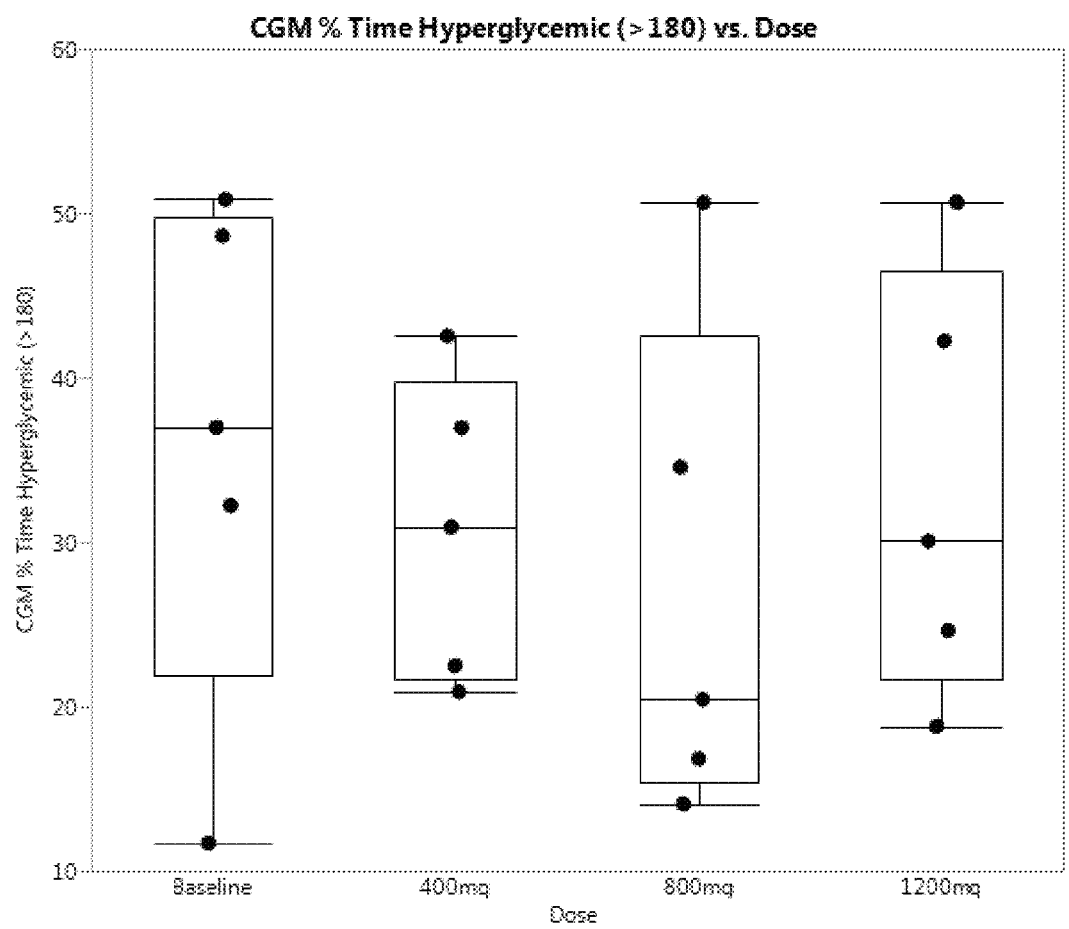
FIG. 4 displays the percentage of time each subject's blood glucose level was greater than 180 mg/dL at each dose (400, 800, and 1200 mg/day of UT-1) and for baseline, where each data point represents the median of four days (days 3-6) at each dose for each subject.

In FIG. 4, the median value of the percentage of time blood glucose levels were greater than 180 mg/dL (hyperglycemia) decreased from baseline (37%) to the 400 mg dose (30.92%), and from the 400 mg dose (30.92%) to the 800 mg dose (20.46%). The data used to prepare FIG. 4 is provided in Table 4.

TABLE 4

Percentage of time (using CGM) blood glucose level is above 180 mg/dL for each subject at baseline and at each dose.

| | | Dose of UT-1 | | |
|---|---|---|---|---|
| Subject | Baseline (%) | 400 mg (%) | 800 mg (%) | 1200 mg (%) |
| 1 | 48.63 | 30.92 | 16.82 | 24.62 |
| 2 | 11.69 | 36.99 | 20.46 | 30.09 |
| 3 | 37 | 20.91 | 50.66 | 42.24 |
| 4 | 50.86 | 42.54 | 34.56 | 50.68 |
| 5 | 32.24 | 22.49 | 14.07 | 18.79 |

Each data point in Table 4 represents the median of four days (days 3-6) at each dose for each subject.

Figure 5:
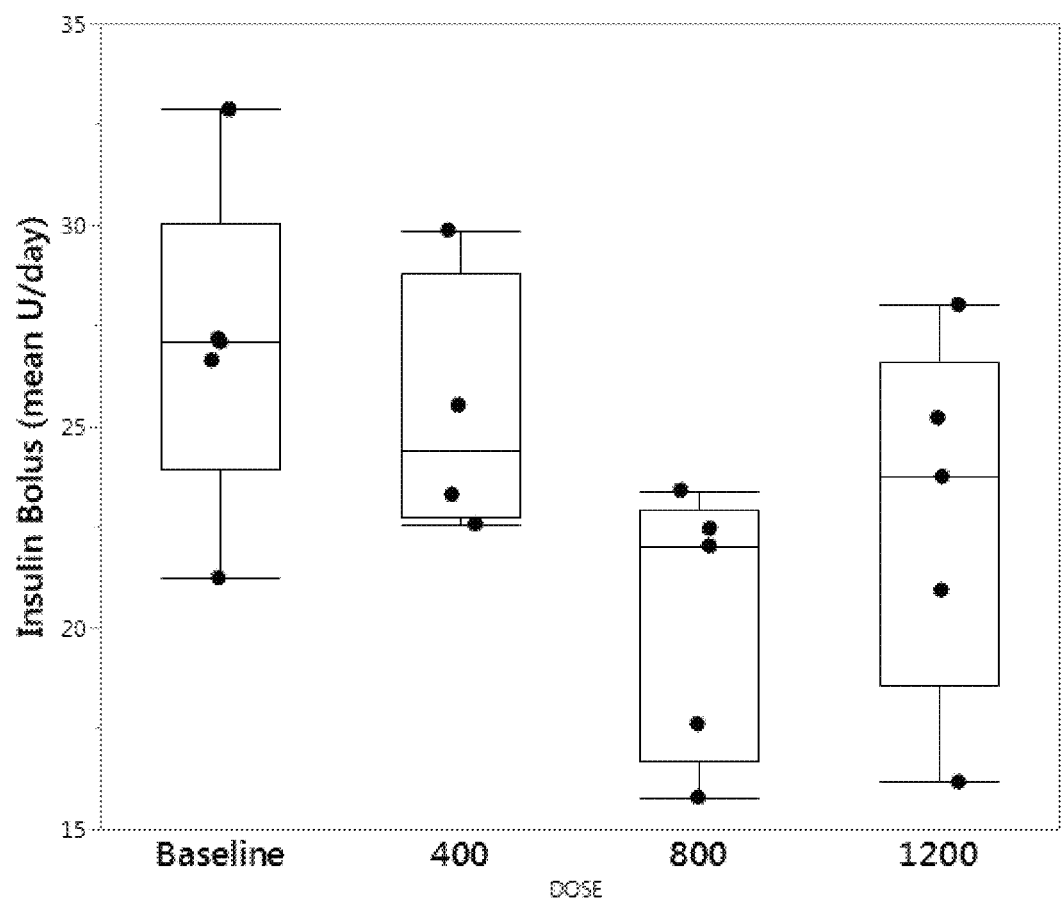
FIG. 5 displays the mean bolus insulin dose (U) per day at each dose (400, 800, and 1200 mg/day of UT-1) and for baseline, where each data point represents the mean of four days (days 3-6) at each dose for each subject.

In FIG. 5, the mean value of bolus insulin dose per day (mean U/day) decreased from baseline (27.1 mean U/day) to 400 mg (25 mean U/day), and from 400 mg to 800 mg (20 mean U/day).

The data used to prepare FIG. 5 is provided in Table 5.

TABLE 5

Mean units of bolus insulin units administered per day for each subject at baseline and at each dose.

| Subject | Baseline (mean U/day) | Dose of UT-1 | | |
|---|---|---|---|---|
| | | 400 mg (mean U/day) | 800 mg (mean U/day) | 1200 mg (mean U/day) |
| 1 | 32.9 | 25.5 | 22 | 28 |
| 2 | 26.7 | 23.3 | 15.8 | 25.2 |
| 3 | 27.1 | 22.6 | 17.6 | 16.2 |
| 4 | 27.2 | 29.9 | 23.4 | 23.8 |
| 5 | 21.3 | Not measured | 22.5 | 20.9 |

Each data point in Table 5 represents the mean of four days (days 3-6) at each dose for each subject.

Figure 6:
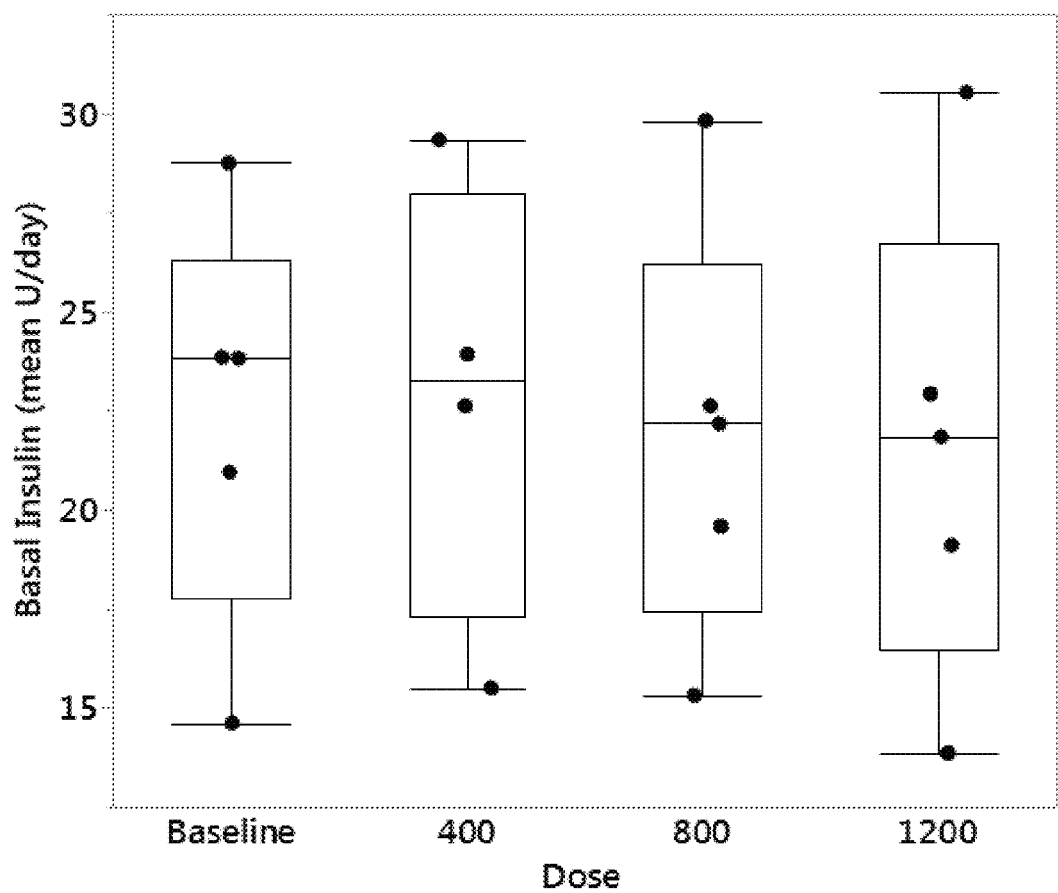
FIG. 6 displays the mean basal insulin dose (U) per day at each dose (400, 800, and 1200 mg/day of UT-1) and for baseline, where each data point represents the mean of four days (days 3-6) at each dose for each subject.

The data used to prepare FIG. 6 is provided in Table 6.

TABLE 6

Mean units of basal insulin units administered per day for each subject at baseline and at each dose.

| Subject | Baseline (mean U/day) | Dose of UT-1 | | |
|---|---|---|---|---|
| | | 400 mg (mean U/day) | 800 mg (mean U/day) | 1200 mg (mean U/day) |
| 1 | 28.8 | 29.3 | 29.8 | 30.5 |
| 2 | 21.0 | 22.6 | 22.2 | 19.1 |
| 3 | 23.8 | 23.9 | 22.6 | 22.9 |
| 4 | 14.6 | 15.5 | 15.3 | 13.9 |
| 5 | 23.9 | Not measured | 19.6 | 21.8 |

Each data point in Table 6 represents the mean of four days (days 3-6) at each dose for each subject.

Example 2—Study Design

A multi-center double-blind placebo-controlled study with a 2-week single-blind placebo run-in period to evaluate UT-1 as a potential adjunctive treatment to insulin therapy for T1DM was conducted. The study examined the response in 20 adult patients with T1DM who were using a continuous glucose monitoring (CGM) device and insulin delivered by continuous subcutaneous insulin infusion (CSII) dosed once daily with either placebo or 800 mg UT-1 for up to 12 weeks. The once daily treatment was administered with the morning meal. Safety and assessments labs were collected prior to the placebo-run in period, at Day 1 prior to dosing with blinded study medication, at weeks 2, 4, 6, 8, 12 and at approximately week 13. Insulin pump data and CGM data was collected from the single-blind placebo run-in period to the end of dosing. A quality of life and treatment satisfaction questionnaires were also used. Insulin was adjusted by patients as required to maintain glycemic control.

Results

The baseline mean HbA1c for the groups treated with UT-1 and placebo was 7.3% and 7.4%, respectively. Patients treated with UT-1 (n=8) showed a statistically significant mean reduction in HbA1c of 0.6% at 12 weeks (ending at HbA1c of between 6.7-6.8% at 12 weeks), while the group treated with placebo (n=11) showed a mean increase in HbA1c of 0.1% (ending at HbA1c of 7.5% at 12 weeks), resulting in a mean difference of 0.7% in the UT-1 group relative to the placebo group (p=0.03). At the same time, trends toward decreased insulin usage were observed in the group treated with UT-1.

Patients in this study received insulin adjustments to optimize glucose levels. As a result, the primary analysis included a responder analysis in which a 'treatment responder' was defined as a patient who had a decrease in HbA1c at Week 12, no abnormal lactate (greater than 20 mg/dL) or abnormal metabolic ketones (greater than 4.17 mg/dL of BHB) detected in blood or urine during the study, and no increased time in Level 2 hypoglycemia (blood glucose <54 mg/dl). Of all study patients, there was a greater proportion of responders in the group treated with UT-1 (75%) than in the placebo group (9%) (p=0.006). Consistent with the treatment responder results, abnormal levels of metabolic ketones were observed in plasma or urine in 63% of patients on placebo vs. 13% of patients treated with UT-1.

UT-1 was well tolerated with similar incidences of treatment-emergent adverse events overall and by system organ class. The study had no serious adverse event reported. The study also had no report of diabetic ketoacidosis or severe hypoglycemia.

What is claimed is:

1. A method of lowering glycated hemoglobin levels in a human subject having type 1 diabetes, the method comprising administering to the human subject 400 mg/day to 1200 mg/day of {2-[3-cyclohexyl-3-(trans-4-propoxy-cyclohexyl)-ureido]-thiazol-5-ylsulfanyl}-acetic acid or a pharmaceutically acceptable salt thereof in combination with insulin or an insulin analog, wherein the {2-[3-cyclohexyl-3-(trans-4-propoxy-cyclohexyl)-ureido]-thiazol-5-ylsulfanyl}-acetic acid or a pharmaceutically acceptable salt thereof is orally administered one time a day, and wherein the incidence of hypoglycemic events in the human subject is reduced.

2. The method of claim 1, wherein the glycated hemoglobin is HbA1c, and wherein the method comprises lowering HbA1c levels in the human subject by at least 0.3 percentage points.

3. The method of claim 1, wherein the administering comprises administering the insulin or the insulin analog orally, subcutaneously, or by injection.

4. The method of claim 1, wherein the {2-[3-cyclohexyl-3-(trans-4-propoxy-cyclohexyl)-ureido]-thiazol-5-ylsulfanyl}-acetic acid or a pharmaceutically acceptable salt thereof is administered in a solid dosage form.

5. The method of claim 4, wherein the solid dosage form is a tablet or capsule.

6. The method of claim 4, wherein the solid dosage form comprises 400-450 mg of {2-[3-cyclohexyl-3-(trans-4-propoxy-cyclohexyl)-ureido]-thiazol-5-ylsulfanyl}-acetic acid or a pharmaceutically acceptable salt thereof.

7. The method of claim 1, wherein the glycated hemoglobin is HbA1c.

8. The method of claim 1, wherein the insulin analog is a rapid-acting insulin, regular- or short-acting insulin, intermediate-acting insulin, a long-acting insulin, or a combination thereof.

9. The method of claim 1, wherein the insulin analog comprises a short-acting insulin, intermediate-acting insulin, or a long-acting insulin.

10. The method of claim 9, wherein the insulin analog comprises a combination of an intermediate-acting insulin and a long-acting insulin.

11. The method of claim 1, wherein the insulin analog is insulin lispro, insulin aspart, insulin glulisine, isophane insulin, insulin zinc, insulin glargine, insulin detemir, or any combination thereof.

12. The method of claim 1, wherein an insulin analog is administered, and the insulin analog is insulin lispro or insulin aspart.

13. The method of claim 1, wherein the incidence of diabetic ketosis events in the human subject is reduced.

* * * * *